US005756461A

United States Patent [19]

Stephens

[11] Patent Number: 5,756,461
[45] Date of Patent: May 26, 1998

[54] METHODS FOR TREATING DIABETES

[75] Inventor: Thomas Wesley Stephens, Indianapolis, Ind.

[73] Assignee: Eli Lilly and Company, Indianapolis, Ind.

[21] Appl. No.: 678,369

[22] Filed: Jun. 28, 1996

Related U.S. Application Data

[60] Provisional application No. 60/000,718 Jun. 30, 1995.
[51] Int. Cl.$^6$ .................... A61K 38/00; A61K 38/16; C07K 14/00
[52] U.S. Cl. .................. 514/12; 514/866; 530/324
[58] Field of Search ........................ 514/12, 866

[56] References Cited

FOREIGN PATENT DOCUMENTS

WO 96/05309  2/1996  WIPO .

OTHER PUBLICATIONS

MacDougald et al. Regulated expression of the obese gene product (leptin) in white adipose tissue and 3T3-L1 adipocytes. Proc. Natl. Acad. Sci. Sep. 1995, vol. 92, pp. 9034-9037.
HE et al. The Mouse obese Gene. The Journal of Biological chemistry. 1 Dec. 1995, vol. 270, No. 48, pp. 28887-28891.
Berkow et al. Merck Manual, New Jersey: Merck Research Laboratories. 1992, vol. 16, pp. 1106-1109.
Chem. Abstract 94-304407/38, Nagata Sangyo Co. Ltd. (Mar. 29, 1993).
Zhang, et al., "Positional cloning of the mouse obese gene and its human homologue", *Nature,* 372:1, 425-432 (Dec. 1, 1994).
Rink. "In Search of a satiety factor", *Nature* 372:1, 406-407 (Dec. 1, 1994).
Flam, "Obesity Gene Discovery May Help Sove Weighty Problem", *Science* 266, 1477-1478 (Dec. 2, 1994).
Hodgson, "Obesity" Where Less is More, *Bio/Technology* 13, 1060-1063 (Oct. 1995).
Stephens, et al., "The role of neuropeptide Y in the antiobesity action of the obese gene product", *Nature* 377, 530-532 (Oct. 12, 1995).

Masuzaki, et al., "Human Obese Gene Expression", *Diabetes,* 44 855-858 (Jul. 1995).
Barinaga. "Obese" Protein Slims Mice, Science 269, 475,-476 (Jul. 28, 1995).
Weigle, et al., "Recominant ob Protein Reduces feeding and Body Weight in the ob/ob Mouse", *J. Clin. Invest.* 96 2065-2070 (Oct. 1995).
Murakami, et al., "Cloning of Rat Obese cDNA and Its Expression in Obese Rats$^+$",*Biochemical and Biophysical Research Communications* 209:3 944-952 (Apr. 26, 1995).
Campfield, et al., "Recominant Mouse OB Protein: Evidence for a Peripheral Signal Linking Adiposity and Central Neural Networks",*Science* 269, 546-549 (Jul. 28, 1995).
Considine, et al., "Evidence Against Either a Premature Stop Codon or the Absence of Obese Gene mRNA in Human Obesity", *J. Clin. Invest.* 95, 2985-2988 (Jun. 1995).
Pelleymounter, et al., "Effects of the Obese Gene Product on Body Weight Regulation in ob/ob Mice", *Science* 269, 540-543 (Jul. 28, 1995).
Halaas, et al., "Weight-Reducing Effects of the Plasma Protein Encoded by the obese Gene", *Science* 269, 543-546 (Jul. 18, 1995).
Zarjevski, et al., "Chronic Intracerebroventricular Neuropeptide-Y Administration to Normal Rats Mimics Hormonal and Metabolic Changes of Obesity", *Endocrinology,* vol. 133, No. 4 (1993).
Jeanrenaud, B., "An hypothesis on the aetiology of obesity: dysfunction of the central nervous system as a primary cause", *Diabetologia* (1985) 28:502-513.
Jeanrenaud, B., Central nervous system and peripheral abnormalities: clues to the understanding of obesity and NIDDM, Diabetologia (1994) 37 [Suppl 2]: S169-S178.
Jeanrenaud, B., "Neuroendocrine and Metabolic Basis of Type II Diabetes as Studied in Animal Models", Diabetes Metabolism Reviews, vol. 4 No. 6, 603-614 (1988).

*Primary Examiner*—Cecilia J. Tsang
*Assistant Examiner*—Michael Borin
*Attorney, Agent, or Firm*—Ronald S. Maciak; David E. Boone

[57] ABSTRACT

This invention describes methods of treating or preventing diabetes in obese type II diabetic patients. Specifically, methods of treating obese type II diabetics with varying levels of endogenous circulating leptin are claimed.

7 Claims, No Drawings

METHODS FOR TREATING DIABETES

CROSS REFERENCE

This application claims the benefit of U.S. Provisional Application Ser. No. 60/000,718 filed Jun. 30, 1995.

FIELD OF THE INVENTION

The present invention relates to the field of human medicine, particularly the treatment of diabetes. Most specifically, the invention relates to a method for treating obese, type II diabetics whose endogenous leptin levels are abnormally low or high.

BACKGROUND OF THE INVENTION

Diabetes mellitus is a metabolic disorder characterized by the failure of body tissues to store carbohydrates at the normal rate. Resistance to the action of insulin is the most important factor to type II diabetes. When this resistance exceeds the capacity of the beta cells to produce insulin, a person becomes diabetic. During the last 70 years people suffering from diabetes have been greatly aided by receiving controlled amounts of insulin.

Obesity, particularly upper body obesity, is often associated with non-insulin-dependent diabetes mellitus (NIDDM). These so called type II diabetics do not have an absolute requirement for insulin as their beta cells are able to secrete insulin, albeit often at diminished levels. In addition such patients are often obese and may demonstrate an inability to respond to insulin.

It is well known that a regimen of diet and exercise leading to weight loss is the best approach for treating obese type II diabetics. Unfortunately, these regimens are usually unsuccessful. Failure to loss weight may be due to genetically inherited factors that contribute to increased appetite, a preference for high calorie foods, reduced physical activity, and an increased lipogenic metabolism. People inheriting such genetic predispositions are prone to obesity and often become type II diabetics, regardless of their efforts to combat the condition.

The ob/ob mouse is a model of obesity and diabetes that is known to carry an autosomal recessive trait linked to a mutation in the sixth chromosome. Yiying zhang and co-workers published the positional cloning of the mouse gene (ob) linked with this condition. Yiying Zhang et al. *Nature* 372: 425–32 (1994). This report disclosed a gene coding for a 167 amino acid protein (hereinafter leptin) with a 21 amino acid signal peptide that is exclusively expressed in adipose tissue.

Physiologists have postulated for years that, when a mammal overeats, the resulting excess fat signals to the brain that the body is obese which, in turn, causes the body to eat less and burn more fuel. G. R. Hervey, *Nature (London)*, 227: 629–631 (1969). This model of feedback inhibition is supported by parabiotic experiments, which implicate a circulating hormone controlling adiposity.

Based on recent in vivo experiments conducted under the inventor's supervision, leptin has now been shown to be an adiposity regulating hormone. Most importantly however, blood parameters monitored during these experiments quite unexpectedly demonstrated that treatment with leptin totally ameliorated the diabetic state of the research animals.

Moreover, circulating levels of leptin in obese individuals have been shown to vary widely. Consequently, it is now believed that certain subpopulations of obese type II diabetics are particularly amenable to treatment with leptin. Pharmacological agents which are biologically active and mimic the activity of leptin are therefore useful for treating obese type II diabetics, particularly those with abnormal levels of circulating leptin.

SUMMARY OF THE INVENTION

A method of treating or preventing diabetes mellitus which comprises administering to an obese type II diabetic an effective amount of leptin, leptin mimetic, fragment thereof, or a pharmaceutically acceptable salt thereof is claimed. In a preferred embodiment, the invention includes methods for treating obese type II diabetics having abnormal endogenous levels of circulating leptin.

DETAILED DESCRIPTION OF THE INVENTION

The terms and abbreviations used in this document have their normal meanings unless otherwise designated. For example "°C." refers to degrees Celsius; "N" refers to normal or normality; "mmol" refers to millimole or millimoles; "g" refers to gram or grams; "ml" means milliliter or milliliters; "M" refers to molar or molarity; "μg" refers to microgram or micrograms; and "μl" refers to microliter or microliters.

All amino acid or protein sequences, unless otherwise designated, are written commencing with the amino terminus ("N-terminus") and concluding with the carboxy terminus ("C-terminus"). "Base pair" or "bp" as used herein refers to DNA or RNA. The abbreviations A,C,G, and T correspond to the 5'-monophosphate forms of the deoxyribonucleosides (deoxy)adenine, (deoxy)cytidine, (deoxy)guanine, and (deoxy)thymine, respectively, when they occur in DNA molecules. The abbreviations U,C,G, and T correspond to the 5'-monophosphate forms of the ribonucleosides uracil, cytidine, guanine, and thymine, respectively when they occur in RNA molecules. In double stranded DNA, base pair may refer to a partnership of A with T or C with G. In a DNA/RNA, heteroduplex base pair may refer to a partnership of A with U or C with G. (See the definition of "complementary", infra.)

The terms "digestion" or "restriction" of DNA refers to the catalytic cleavage of the DNA with a restriction enzyme that acts only at certain sequences in the DNA ("sequence-specific endonucleases"). The various restriction enzymes used herein are commercially available and their reaction conditions, cofactors, and other requirements were used as would be known to one of ordinary skill in the art. Appropriate buffers and substrate amounts for particular restriction enzymes are specified by the manufacturer or can be readily found in the literature.

"Ligation" refers to the process of forming phosphodiester bonds between two double stranded nucleic acid fragments. Unless otherwise provided, ligation may be accomplished using known buffers and conditions with a DNA ligase, such as T4 DNA ligase.

The term "plasmid" refers to an extrachromosomal (usually) self-replicating genetic element. Plasmids are generally designated by a lower case "p" preceded and/or followed by letters and/or numbers. The starting plasmids herein are either commercially available, publicly available on an unrestricted basis, or can be constructed from available plasmids in accordance with published procedures. In addition, equivalent plasmids to those described are known in the art and will be apparent to the ordinarily skilled artisan.

The term "reading frame" means the nucleotide sequence from which translation occurs "read" in triplets by the translational apparatus of transfer RNA (tRNA) and ribosomes and associated factors, each triplet corresponding to a particular amino acid. A base pair insertion or deletion (termed a frameshift mutation) may result in two different proteins being coded for by the same DNA segment. To insure against this, the triplet codons corresponding to the desired polypeptide must be aligned in multiples of three from the initiation codon, i.e. the correct "reading frame" being maintained.

The term "expression vector system" as used herein refers to a recombinant DNA expression vector in combination with one or more trans-acting factors that specifically influence transcription, stability, or replication of the recombinant DNA expression vector. The trans-acting factor may be expressed from a co-transfected plasmid, virus, or other extrachromosomal element, or may be expressed from a gene integrated within the chromosome.

"Transcription" as used herein refers to the process whereby information contained in a nucleotide sequence of DNA is transferred to a complementary RNA sequence.

The term "transfection" as used herein refers to the taking up of an expression vector by a host cell whether or not any coding sequences are in fact expressed. Numerous methods of transfection are known to the ordinarily skilled artisan, for example, calcium phosphate co-precipitation, and electroporation. Successful transfection is generally recognized when any indication of the operation of this vector occurs within the host cell.

The term "transformation" as used herein means the introduction of DNA into an organism so that the DNA is replicable, either as an extrachromosomal element or by chromosomal integration. Methods of transforming bacterial and eukaryotic hosts are well known in the art, many of which methods, such as nuclear injection, protoplast fusion or by calcium treatment using calcium chloride are summarized in J. Sambrook, et al., MOLECULAR CLONING: A LABORATORY MANUAL, (1989).

The term "translation" as used herein refers to the process whereby the genetic information of messenger RNA is used to specify and direct the synthesis of a polypeptide chain.

The term "vector" as used herein refers to a nucleic acid compound used for the transformation of cells in gene manipulation bearing polynucleotide sequences corresponding to appropriate protein molecules which when combined with appropriate control sequences confer specific properties on the host cell to be transformed. Plasmids, viruses, and bacteriophage are suitable vectors. Artificial vectors are constructed by cutting and joining DNA molecules from different sources using restriction enzymes and ligases. The term "vector" as used herein includes Recombinant DNA cloning vectors and Recombinant DNA expression vectors.

The terms "complementary" or "complementarity" as used herein refers to pair of bases, purines and pyrimidines, that associate through hydrogen bonding in double stranded nucleic acid. The following base pairs are complementary: guanine and cytosine; adenine and thymine; and adenine and uracil.

The term "hybridization" as used herein refers to a process in which a strand of nucleic acid joins with a complementary strand through base pairing. The conditions employed in the hybridization of two non-identical, but very similar, complementary nucleic acids varies with the degree of complementarity of the two strands and the length of the strands. Such techniques and conditions are well known to practitioners in this field.

"Isolated amino acid sequence" refers to any amino acid sequence, however constructed or synthesized, which is locationally distinct from the naturally occurring sequence.

"Isolated DNA compound" refers to any DNA sequence, however constructed or synthesized, which is locationally distinct from its natural location in genomic DNA.

"Isolated nucleic acid compound" refers to any RNA or DNA sequence, however constructed or synthesized, which is locationally distinct from its natural location.

A "primer" is a nucleic acid fragment which functions as an initiating substrate for enzymatic or synthetic elongation.

The term "promoter" refers to a DNA sequence which directs transcription of DNA to RNA.

A "probe" as used herein is a nucleic acid compound or a fragment thereof which hybridizes with a complementary nucleic acid compound.

The term "stringency" refers to a set of hybridization conditions which may be modulated to vary the degree to which probes bind their complementary DNA strands.

The term "PCR" as used herein refers to the widely-known polymerase chain reaction employing a thermally-stable polymerase.

The phrase "reading frame" as used herein refers to the nucleotide sequence from which translation occurs "read" in triplets by the translational apparatus of tRNA, ribosomes and associated factors, each triplet corresponding to a particular amino acid. Because each triplet is distinct and of the same length, the coding sequence must be a multiple of three. A base pair insertion or deletion (termed a frameshift mutation) may result in two different proteins being coded for by the same DNA segment. To insure against this, the triplet codons corresponding to the desired polypeptide must be aligned in multiples of three from the initiation codon, i.e. the correct "reading frame" must be maintained. In the creation of fusion proteins containing a chelating peptide, the reading frame of the DNA sequence encoding the structural protein must be maintained in the DNA sequence encoding the chelating peptide.

The term "treating" describes the management and care of a patient for the purpose of combating the disease, condition, or disorder and includes the administration of leptin to prevent the onset of the symptoms or complications, alleviating the symptoms or complications, or eliminating the disease, condition, or disorder. Treating obese type II diabetics, for example, may include but is not limited to lowering elevated blood glucose and insulin levels, as well as lowering triglyceride and corticosterone levels in patients.

Obese—refers to a condition in which the individual has a body mass index (BMI) of greater than 27 kilograms per square meter.

Leptin—refers to the protein produced from the obesity gene following transcription and deletions of introns, translation to a protein and processing to the mature protein with secretory signal peptide removed, e.g., from the N-terminal valine-proline to the C-terminal cysteine of the mature protein. The mouse obesity protein and human obesity protein is published in zhang et al, Supra. The rat obesity protein is published in Murakami et al., Biochemical and Biophysical Research Comm. 209(3): 944–52 (1995). In the human, murine and rat obesity protein the Cys associated with di-sulfide formation is positions 96 and 145. However, particularly with the murine and human obesity protein, a desGln(28) variant has been observed. Hense, the Cys residues associated with di-sulfide bond formation may be at positions 95 or 96 and at position 145 or 146. Leptin may also be referred to throughout this specification as obesity protein, OB, or ob gene product. Native leptin therefore includes SEQ ID NOs:1–6 as follows.

Murine Leptin
SEQ ID NO: 1

Val Pro Ile Gln Lys Val Gln Asp Asp Thr Lys Thr Leu Ile Lys Thr
1               5                       10                      15

Ile Val Thr Arg Ile Asn Asp Ile Ser His Thr Xaa Ser Val Ser Ser
            20                      25                      30

Lys Gln Lys Val Thr Gly Leu Asp Phe Ile Pro Gly Leu His Pro Ile
            35                      40                      45

Leu Thr Leu Ser Lys Met Asp Gln Thr Leu Ala Val Tyr Gln Gln Ile
            50                      55                      60

Leu Thr Ser Met Pro Ser Arg Asn Val Ile Gln Ile Ser Asn Asp Leu
65                      70                      75                      80

Glu Asn Leu Arg Asp Leu Leu His Val Leu Ala Phe Ser Lys Ser Cys
            85                      90                      95

His Leu Pro Gln Ala Ser Gly Leu Glu Thr Leu Glu Ser Leu Gly Gly
            100                     105                     110

Val Leu Glu Ala Ser Gly Tyr Ser Thr Glu Val Val Ala Leu Ser Arg
            115                     120                     125

Leu Gln Gly Ser Leu Gln Asp Met Leu Gln Gln Leu Asp Leu Ser Pro
            130                     135                     140

Gly Cys
145 wherein:

Xaa at position 28 is Gln or absent.

Porcine Leptin
SEQ ID NO: 2

Val Pro Ile Trp Arg Val Gln Asp Asp Thr Lys Thr Leu Ile Lys Thr
1               5                       10                      15

Ile Val Thr Arg Ile Ser Asp Ile Ser His Met Gln Ser Val Ser Ser
            20                      25                      30

Lys Gln Arg Val Thr Gly Leu Asp Phe Ile Pro Gly Leu His Pro Val
            35                      40                      45

Leu Ser Leu Ser Lys Met Asp Gln Thr Leu Ala Ile Tyr Gln Gln Ile
            50                      55                      60

Leu Thr Ser Leu Pro Ser Arg Asn Val Ile Gln Ile Ser Asn Asp Leu
65                      70                      75                      80

Glu Asn Leu Arg Asp Leu Leu His Leu Leu Ala Ser Ser Lys Ser Cys
            85                      90                      95

Pro Leu Pro Gln Ala Arg Ala Leu Glu Thr Leu Glu Ser Leu Gly Gly
            100                     105                     110

Val Leu Glu Ala Ser Leu Tyr Ser Thr Glu Val Val Ala Leu Ser Arg
            115                     120                     125

Leu Gln Gly Ala Leu Gln Asp Met Leu Arg Gln Leu Asp Leu Ser Pro
            130                     135                     140

Gly Cys
145

Bovine Leptin
SEQ ID NO: 3

Val Pro Ile Cys Lys Val Gln Asp Asp Thr Lys Thr Leu Ile Lys Thr
1               5                       10                      15

Ile Val Thr Arg Ile Asn Asp Ile Ser His Thr Xaa Ser Val Ser Ser
            20                      25                      30

Lys Gln Arg Val Thr Gly Leu Asp Phe Ile Pro Gly Leu His Pro Leu
            35                      40                      45

Leu Ser Leu Ser Lys Met Asp Gln Thr Leu Ala Ile Tyr Gln Gln Ile
            50                      55                      60

Leu Thr Ser Leu Pro Ser Arg Asn Val Val Gln Ile Ser Asn Asp Leu
65                      70                      75                      80

Glu Asn Leu Arg Asp Leu Leu His Leu Leu Ala Ser Ser Lys Ser Cys
            85                      90                      95

Pro Leu Pro Gln Val Arg Ala Leu Glu Ser Leu Glu Ser Leu Gly Val
            100                     105                     110

Val Leu Glu Ala Ser Leu Tyr Ser Thr Glu Val Val Ala Leu Ser Arg
            115                     120                     125

Leu Gln Gly Ser Leu Gln Asp Met Leu Arg Gln Leu Asp Leu Ser Pro
            130                     135                     140

Gly Cys
145 wherein Xaa at position 28 is Gln or absent.

Human Leptin
SEQ ID NO: 4

Val Pro Ile Gln Lys Val Gln Asp Asp Thr Lys Thr Leu Ile Lys Thr
1               5                       10                      15

Ile Val Thr Arg Ile Asn Asp Ile Ser His Xaa Xaa Ser Val Ser Ser
            20                      25                      30

Lys Gln Lys Val Thr Gly Leu Asp Phe Ile Pro Gly Leu His Pro Ile
            35                      40                      45

Leu Thr Leu Ser Lys Met Asp Gln Thr Leu Ala Val Tyr Gln Gln Ile
            50                      55                      60

Leu Thr Ser Met Pro Ser Arg Asn Val Ile Gln Ile Ser Asn Asp Leu
65                      70                      75                      80

Glu Asn Leu Arg Asp Leu Leu His Val Leu Ala Phe Ser Lys Ser Cys
            85                      90                      95

His Leu Pro Trp Ala Ser Gly Leu Glu Thr Leu Asp Ser Leu Gly Gly
            100                     105                     110

Val Leu Glu Ala Ser Gly Tyr Ser Thr Glu Val Val Ala Leu Ser Arg
            115                     120                     125

Leu Gln Gly Ser Leu Gln Asp Met Leu Trp Gln Leu Asp Leu Ser Pro
            130                     135                     140

145
Gly Cys wherein:

Xaa at position 27 is Thr or Ala; and
Xaa at position 28 is Gln or absent.

Rhesus Leptin
SEQ ID NO:5

Val Pro Ile Gln Lys Val Gln Ser Asp Thr Lys Thr Leu Ile Lys
1               5                       10                      15

Thr Ile Val Thr Arg Ile Asn Asp Ile Ser His Thr Gln Ser Val
                20                      25                      30

Ser Ser Lys Gln Arg Val Thr Gly Leu Asp Phe Ile Pro Gly Leu
            35                      40                      45

His Pro Val Leu Thr Leu Ser Gln Met Asp Gln Thr Leu Ala Ile
            50                      55                      60

Tyr Gln Gln Ile Leu Ile Asn Leu Pro Ser Arg Asn Val Ile Gln
            65                      70                      75

Ile Ser Asn Asp Leu Glu Asn Leu Arg Asp Leu Leu His Leu Leu
            80                      85                      90

```
Ala Phe Ser Lys Ser Cys His Leu Pro Leu Ala Ser Gly Leu Glu
            95              100                 105

Thr Leu Glu Ser Leu Gly Asp Val Leu Glu Ala Ser Leu Tyr Ser
            110             115                 120

Thr Glu Val Val Ala Leu Ser Arg Leu Gln Gly Ser Leu Gln Asp
            125             130                 135

Met Leu Trp Gln Leu Asp Leu Ser Pro Gly Cys
            140             145
```

Rat Leptin
SEQ ID NO:6

```
Val Pro Ile His Lys Val Gln Asp Asp Thr Lys Thr Leu Ile Lys Thr
1               5               10                  15

Ile Val Thr Arg Ile Asn Asp Ile Ser His Thr Gln Ser Val Ser Ala
            20              25                  30

Arg Gln Arg Val Thr Gly Leu Asp Phe Ile Pro Gly Leu His Pro Leu
            35              40                  45

Leu Ser Leu Ser Lys Met Asp Gln Thr Leu Ala Val Tyr Gln Gln Ile
            50              55                  60

Leu Thr Ser Leu Pro Ser Gln Asn Val Leu Gln Ile Ala His Asp Leu
65              70              75                      80

Glu Asn Leu Arg Asp Leu Leu His Leu Leu Ala Phe Ser Lys Ser Cys
            85              90                  95

Ser Leu Pro Gln Thr Arg Gly Leu Gln Lys Pro Glu Ser Leu Asp Gly
            100             105                 110

Val Leu Glu Ala Ser Leu Tyr Ser Thr Glu Val Val Ala Leu Ser Arg
            115             120                 125

Leu Gln Gly Ser Leu Gln Asp Ile Leu Gln Gln Leu Asp Leu Ser Pro
            130             135                 140

Glu Cys
145
```

Leptin mimetics are useful in the presently claimed methods such as those described in Basinski et al., in U.S. application Ser. No. 08/383,638, filed Feb. 6, 1995, and Hanson M. Hsung and Dennis P. Smith, in U.S. application Ser. No. 08/445,305, (Attorney Docket Number X-10179), filed May 19, 1995 herein incorporated by reference and shown in SEQ ID NOs: 7 and 8. More preferred antidiabetic proteins useful in the present invention include the native leptins shown in SEQ ID NOs: 1–6

Those skilled in the art will recognize that certain amino acids are prone to rearrangement. For example, Asp may rearrange to aspartimide and isoasparigine as described in I. Schön, et al., *International Journal of Peptide and Protein Research*, 14: 485–94 (1979) and references cited therein. These rearrangement derivatives are included within the scope of the present invention.

In addition to the above identified protein sequences, it is frequently considered expeditious to prepare such anti diabetic proteins with a one or two amino acid leader sequence, especially with a methionine containing leader. Two frequently employed leaders are Met-Arg and Met-Asp. Such proteins may be identified infra as Met-Arg-leptin or Met-Asp-leptin or may be identified by Met-Arg-SEQ ID NO:X, where X is 1 to 8.

Leptin mimetics and fragments are also useful in the methods of the present invention. Leptin mimetics and fragments are generally defined as follows:

SEQ ID NO:7

```
Val Pro Ile Gln Lys Val Gln Asp Asp Thr Lys Thr Leu Ile Lys
1               5               10                  15

Thr Ile Val Thr Arg Ile Xaa Asp Ile Ser His Xaa Xaa Ser Val
            20              25                  30

Ser Ser Lys Gln Lys Val Thr Gly Leu Asp Phe Ile Pro Gly Leu
            35              40                  45

His Pro Ile Leu Thr Leu Ser Lys Xaa Asp Gln Thr Leu Ala Val
            50              55                  60

Tyr Gln Gln Ile Leu Thr Ser Xaa Pro Ser Arg Xaa Val Ile Gln
            65              70                  75

Ile Xaa Asn Asp Leu Glu Asn Leu Arg Asp Leu Leu His Val Leu
            80              85                  90

Ala Phe Ser Lys Ser Cys His Leu Pro Trp Ala Ser Gly Leu Glu
            95              100                 105

Thr Leu Asp Ser Leu Gly Gly Val Leu Glu Ala Ser Xaa Tyr Ser
            110             115                 120 thr Glu Val Val Ala Leu Ser Arg Leu Gln Gly Ser Leu Gln Asp
            125             130                 135

145
Met Leu Trp Gln Leu Asp Leu Ser Pro Gly Cys
            140
``` wherein:
Xaa at position 22 is Asn, Asp or Glu;
Xaa at position 27 is Thr or Ala;
Xaa at position 28 is Gln, Glu, or absent;
Xaa at position 54 is Met or Ala;
Xaa at position 68 is Met or Leu;
Xaa at position 72 Asn, Asp or Glu;
Xaa at position 77 is Ser or Ala;
Xaa at position 118 is Gly or Leu;
said protein having at least one substitution selected from the group consisting of:
His at position 97 is replaced with Ser or Pro;
Trp at position 100 is replaced with Gln, Ala or Leu;
Ala at position 101 is replaced with Thr or Val;
Ser at position 102 is replaced with Arg;
Gly at position 103 is replaced with Ala;
Glu at position 105 is replaced with Gln;
Thr at position 106 is replaced with Lys or Ser;
Leu at position 107 is replaced with Pro;
Asp at position 108 is replaced with Glu; or
Gly at position 111 is replaced with Asp.
Preferably, leptin mimetics are as follows:

SEQ ID NO: 8

```
Val Pro Ile Gln Lys Val Gln Asp Asp Thr Lys Thr Leu Ile Lys
1               5               10                  15

Thr Ile Val Thr Arg Ile Asn Asp Ile Ser His Xaa Gln Ser Val
            20              25                  30

Ser Ser Lys Gln Lys Val Thr Gly Leu Asp Phe Ile Pro Gly Leu
            35              40                  45

His Pro Ile Leu Thr Leu Ser Lys Met Asp Gln Thr Leu Ala Val
            50              55                  60

Tyr Gln Gln Ile Leu Thr Ser Met Pro Ser Arg Asn Val Ile Gln
            65              70                  75
```

-continued
SEQ ID NO: 8

Ile Xaa Asn Asp Leu Glu Asn Leu Arg Asp Leu Leu His Val Leu
              80                  85                    90

Ala Phe Ser Lys Ser Cys His Leu Pro Trp Ala Ser Gly Leu Glu
                95                 100                  105

Thr Leu Asp Ser Leu Gly Gly Val Leu Glu Ala Ser Xaa Tyr Ser
               110                 115                  120

Thr Glu Val Val Ala Leu Ser Arg Leu Gln Gly Ser Leu Gln Asp
               125                 130                  135

145
Met Leu Trp Gln Leu Asp Leu Ser Pro Gly Cys
               140 wherein:

Xaa at position 27 is Thr or Ala;

Xaa at position 77 is Ser or Ala;

Xaa at position 118 is Gly or Leu;

said protein having at least one substitution, preferably having one to five substitutions and, most preferably, one to two substitutions selected from the group consisting of:

His at position 97 is replaced with Ser;

Trp at position 100 is replaced with Ala;

Ala at position 101 is replaced with Thr;

Glu at position 105 is replaced with Gln;

Thr at position 106 is replaced with Lys;

Leu at position 107 is replaced with Pro;

Asp at position 108 is replaced with Glu; or

Gly at position 111 is replaced with Asp.

Examples of preferred leptins useful in the present invention include proteins of SEQ ID NO:8, wherein Xaa at position 27 is Thr; Xaa at position 77 is Ser; Xaa at positions 118 is Gly; and the amino acid residues at positions 97, 100, 101, 105, 106, 107, 108, and 111 are as Table I. The native human sequence is provided as a comparison to the proteins employed in the methods of the present invention.

TABLE I

| | Amino Acid Position | | | | | | | |
|---|---|---|---|---|---|---|---|---|
| Compound | 97 | 100 | 101 | 105 | 106 | 107 | 108 | 111 |
| native human | His | Trp | Ala | Glu | Thr | Leu | Asp | Gly |
| 1 | Ser | Trp | Ala | Glu | Thr | Leu | Asp | Gly |
| 2 | His | Gln | Ala | Glu | Thr | Leu | Asp | Gly |
| 3 | His | Trp | Thr | Glu | Thr | Leu | Asp | Gly |
| 4 | His | Trp | Ala | Gln | Thr | Leu | Asp | Gly |
| 5 | His | Trp | Ala | Glu | Lys | Leu | Asp | Gly |
| 6 | His | Trp | Ala | Glu | Thr | Pro | Asp | Gly |
| 7 | His | Trp | Ala | Glu | Thr | Leu | Glu | Gly |
| 8 | His | Trp | Ala | Glu | Thr | Leu | Asp | Asp |
| 9 | Ser | Gln | Ala | Glu | Thr | Leu | Asp | Gly |
| 10 | Ser | Trp | Thr | Glu | Thr | Leu | Asp | Gly |
| 11 | Ser | Trp | Ala | Gln | Thr | Leu | Asp | Gly |
| 12 | Ser | Trp | Ala | Glu | Lys | Leu | Asp | Gly |
| 13 | Ser | Trp | Ala | Glu | Thr | Pro | Asp | Gly |
| 14 | Ser | Trp | Ala | Glu | Thr | Leu | Glu | Gly |
| 15 | Ser | Trp | Ala | Glu | Thr | Leu | Asp | Asp |
| 16 | His | Gln | Thr | Glu | Thr | Leu | Asp | Gly |
| 17 | His | Gln | Ala | Gln | Thr | Leu | Asp | Gly |
| 18 | His | Gln | Ala | Glu | Lys | Leu | Asp | Gly |
| 19 | His | Gln | Ala | Glu | Thr | Pro | Asp | Gly |
| 20 | His | Gln | Ala | Glu | Thr | Leu | Glu | Gly |
| 21 | His | Gln | Ala | Glu | Thr | Leu | Asp | Asp |
| 22 | His | Trp | Thr | Gln | Thr | Leu | Asp | Gly |
| 23 | His | Trp | Thr | Glu | Lys | Leu | Asp | Gly |

TABLE I-continued

| | Amino Acid Position | | | | | | | |
|---|---|---|---|---|---|---|---|---|
| Compound | 97 | 100 | 101 | 105 | 106 | 107 | 108 | 111 |
| 24 | His | Trp | Thr | Glu | Thr | Pro | Asp | Gly |
| 25 | His | Trp | Thr | Glu | Thr | Leu | Glu | Gly |
| 26 | His | Trp | Thr | Glu | Thr | Leu | Asp | Asp |
| 27 | His | Trp | Ala | Gln | Lys | Leu | Asp | Gly |
| 28 | His | Trp | Ala | Gln | Thr | Pro | Asp | Gly |
| 29 | His | Trp | Ala | Gln | Thr | Leu | Glu | Gly |
| 30 | His | Trp | Ala | Gln | Thr | Leu | Asp | Asp |
| 31 | His | Trp | Ala | Glu | Lys | Pro | Asp | Gly |
| 32 | His | Trp | Ala | Glu | Lys | Leu | Glu | Gly |
| 33 | His | Trp | Ala | Glu | Lys | Leu | Asp | Asp |
| 34 | His | Trp | Ala | Glu | Thr | Pro | Glu | Gly |
| 35 | His | Trp | Ala | Glu | Thr | Pro | Asp | Asp |
| 36 | His | Trp | Ala | Glu | Thr | Leu | Glu | Asp |
| 37 | Ser | Gln | Thr | Glu | Thr | Leu | Asp | Gly |
| 38 | Ser | Gln | Ala | Gln | Thr | Leu | Asp | Gly |
| 39 | Ser | Gln | Ala | Glu | Lys | Leu | Asp | Gly |
| 40 | Ser | Gln | Ala | Glu | Thr | Pro | Asp | Gly |
| 41 | Ser | Gln | Ala | Glu | Thr | Leu | Glu | Gly |
| 42 | Ser | Gln | Ala | Glu | Thr | Leu | Asp | Asp |
| 43 | Ser | Trp | Thr | Gln | Thr | Leu | Asp | Gly |
| 44 | Ser | Trp | Thr | Glu | Lys | Leu | Asp | Gly |
| 45 | Ser | Trp | Thr | Glu | Thr | Pro | Asp | Gly |
| 46 | Ser | Trp | Thr | Glu | Thr | Leu | Glu | Gly |
| 47 | Ser | Trp | Thr | Glu | Thr | Leu | Asp | Asp |
| 48 | Ser | Trp | Ala | Gln | Lys | Leu | Asp | Gly |
| 49 | Ser | Trp | Ala | Gln | Thr | Pro | Asp | Gly |
| 50 | Ser | Trp | Ala | Gln | Thr | Leu | Glu | Gly |
| 51 | Ser | Trp | Ala | Gln | Thr | Leu | Asp | Asp |
| 52 | Ser | Trp | Ala | Glu | Lys | Pro | Asp | Gly |
| 53 | Ser | Trp | Ala | Glu | Lys | Leu | Glu | Gly |
| 54 | Ser | Trp | Ala | Glu | Lys | Leu | Asp | Asp |
| 55 | Ser | Trp | Ala | Glu | Thr | Pro | Glu | Gly |
| 56 | Ser | Trp | Ala | Glu | Thr | Pro | Asp | Asp |
| 57 | Ser | Trp | Ala | Glu | Thr | Leu | Glu | Asp |
| 58 | His | Gln | Thr | Gln | Thr | Leu | Asp | Gly |
| 59 | His | Gln | Thr | Glu | Lys | Leu | Asp | Gly |
| 60 | His | Gln | Thr | Glu | Thr | Pro | Asp | Gly |
| 61 | His | Gln | Thr | Glu | Thr | Leu | Glu | Gly |
| 62 | His | Gln | Thr | Glu | Thr | Leu | Asp | Asp |
| 63 | His | Gln | Ala | Gln | Lys | Leu | Asp | Gly |
| 64 | His | Gln | Ala | Gln | Thr | Pro | Asp | Gly |
| 65 | His | Gln | Ala | Gln | Thr | Leu | Glu | Gly |
| 66 | His | Gln | Ala | Gln | Thr | Leu | Asp | Asp |
| 67 | His | Gln | Ala | Glu | Lys | Pro | Asp | Gly |
| 68 | His | Gln | Ala | Glu | Lys | Leu | Glu | Gly |
| 69 | His | Gln | Ala | Glu | Lys | Leu | Asp | Asp |
| 70 | His | Gln | Ala | Glu | Thr | Pro | Glu | Gly |
| 71 | His | Gln | Ala | Glu | Thr | Pro | Asp | Asp |
| 72 | His | Gln | Ala | Glu | Thr | Leu | Glu | Asp |
| 73 | His | Trp | Thr | Gln | Lys | Leu | Asp | Gly |
| 74 | His | Trp | Thr | Gln | Thr | Pro | Asp | Gly |
| 75 | His | Trp | Thr | Gln | Thr | Leu | Glu | Gly |
| 76 | His | Trp | Thr | Gln | Thr | Leu | Asp | Asp |
| 77 | His | Trp | Thr | Glu | Lys | Pro | Asp | Gly |
| 78 | His | Trp | Thr | Glu | Lys | Leu | Glu | Gly |
| 79 | His | Trp | Thr | Glu | Lys | Leu | Asp | Asp |
| 80 | His | Trp | Thr | Glu | Thr | Pro | Glu | Gly |
| 81 | His | Trp | Thr | Glu | Thr | Pro | Asp | Asp |
| 82 | His | Trp | Thr | Glu | Thr | Leu | Glu | Asp |
| 83 | His | Trp | Ala | Gln | Lys | Pro | Asp | Gly |
| 84 | His | Trp | Ala | Gln | Lys | Leu | Glu | Gly |
| 85 | His | Trp | Ala | Gln | Lys | Leu | Asp | Asp |
| 86 | His | Trp | Ala | Gln | Thr | Pro | Glu | Gly |
| 87 | His | Trp | Ala | Gln | Thr | Pro | Asp | Asp |
| 88 | His | Trp | Ala | Gln | Thr | Leu | Glu | Asp |
| 89 | His | Trp | Ala | Glu | Lys | Pro | Glu | Gly |
| 90 | His | Trp | Ala | Glu | Lys | Pro | Asp | Asp |
| 91 | His | Trp | Ala | Glu | Lys | Leu | Glu | Asp |
| 92 | His | Trp | Ala | Glu | Thr | Pro | Glu | Asp |
| 93 | Ser | Gln | Thr | Gln | Thr | Leu | Asp | Gly |
| 94 | Ser | Gln | Thr | Glu | Lys | Leu | Asp | Gly |
| 95 | Ser | Gln | Thr | Glu | Thr | Pro | Asp | Gly |
| 96 | Ser | Gln | Thr | Glu | Thr | Leu | Glu | Gly |
| 97 | Ser | Gln | Thr | Glu | Thr | Leu | Asp | Asp |
| 98 | Ser | Gln | Ala | Gln | Lys | Leu | Asp | Gly |

TABLE I-continued

| Compound | 97 | 100 | 101 | 105 | 106 | 107 | 108 | 111 |
|---|---|---|---|---|---|---|---|---|
| 99 | Ser | Gln | Ala | Gln | Thr | Pro | Asp | Gly |
| 100 | Ser | Gln | Ala | Gln | Thr | Leu | Glu | Gly |
| 101 | Ser | Gln | Ala | Gln | Thr | Leu | Asp | Asp |
| 102 | Ser | Gln | Ala | Glu | Lys | Pro | Asp | Gly |
| 103 | Ser | Gln | Ala | Glu | Lys | Leu | Glu | Gly |
| 104 | Ser | Gln | Ala | Glu | Lys | Leu | Asp | Asp |
| 105 | Ser | Gln | Ala | Glu | Thr | Pro | Glu | Gly |
| 106 | Ser | Gln | Ala | Glu | Thr | Pro | Asp | Asp |
| 107 | Ser | Gln | Ala | Glu | Thr | Leu | Glu | Asp |
| 108 | Ser | Trp | Thr | Gln | Lys | Leu | Asp | Gly |
| 109 | Ser | Trp | Thr | Gln | Thr | Pro | Asp | Gly |
| 110 | Ser | Trp | Thr | Gln | Thr | Leu | Glu | Gly |
| 111 | Ser | Trp | Thr | Gln | Thr | Leu | Asp | Asp |
| 112 | Ser | Trp | Thr | Glu | Lys | Pro | Asp | Gly |
| 113 | Ser | Trp | Thr | Glu | Lys | Leu | Glu | Gly |
| 114 | Ser | Trp | Thr | Glu | Lys | Leu | Asp | Asp |
| 115 | Ser | Trp | Thr | Glu | Thr | Pro | Glu | Gly |
| 116 | Ser | Trp | Thr | Glu | Thr | Pro | Asp | Asp |
| 117 | Ser | Trp | Thr | Glu | Thr | Leu | Glu | Asp |
| 118 | Ser | Trp | Ala | Gln | Lys | Pro | Asp | Gly |
| 119 | Ser | Trp | Ala | Gln | Lys | Leu | Glu | Gly |
| 120 | Ser | Trp | Ala | Gln | Lys | Leu | Asp | Asp |
| 121 | Ser | Trp | Ala | Gln | Thr | Pro | Glu | Gly |
| 122 | Ser | Trp | Ala | Gln | Thr | Pro | Asp | Asp |
| 123 | Ser | Trp | Ala | Gln | Thr | Leu | Glu | Asp |
| 124 | Ser | Trp | Ala | Glu | Lys | Pro | Glu | Gly |
| 125 | Ser | Trp | Ala | Glu | Lys | Pro | Asp | Asp |
| 126 | Ser | Trp | Ala | Glu | Lys | Leu | Glu | Asp |
| 127 | Ser | Trp | Ala | Glu | Thr | Pro | Glu | Asp |
| 128 | His | Gln | Thr | Gln | Lys | Leu | Asp | Gly |
| 129 | His | Gln | Thr | Gln | Thr | Pro | Asp | Gly |
| 130 | His | Gln | Thr | Gln | Thr | Leu | Glu | Gly |
| 131 | His | Gln | Thr | Gln | Thr | Leu | Asp | Asp |
| 132 | His | Gln | Thr | Glu | Lys | Pro | Asp | Gly |
| 133 | His | Gln | Thr | Glu | Lys | Leu | Glu | Gly |
| 134 | His | Gln | Thr | Glu | Lys | Leu | Asp | Asp |
| 135 | His | Gln | Thr | Glu | Thr | Pro | Glu | Gly |
| 136 | His | Gln | Thr | Glu | Thr | Pro | Asp | Asp |
| 137 | His | Gln | Thr | Glu | Thr | Leu | Glu | Asp |
| 138 | His | Gln | Ala | Gln | Lys | Pro | Asp | Gly |
| 139 | His | Gln | Ala | Gln | Lys | Leu | Glu | Gly |
| 140 | His | Gln | Ala | Gln | Lys | Leu | Asp | Asp |
| 141 | His | Gln | Ala | Gln | Thr | Pro | Glu | Gly |
| 142 | His | Gln | Ala | Gln | Thr | Pro | Asp | Asp |
| 143 | His | Gln | Ala | Gln | Thr | Leu | Glu | Asp |
| 144 | His | Gln | Ala | Glu | Lys | Pro | Glu | Gly |
| 145 | His | Gln | Ala | Glu | Lys | Pro | Asp | Asp |
| 146 | His | Gln | Ala | Glu | Lys | Leu | Glu | Asp |
| 147 | His | Gln | Ala | Glu | Thr | Pro | Glu | Asp |
| 148 | His | Trp | Thr | Gln | Lys | Pro | Asp | Gly |
| 149 | His | Trp | Thr | Gln | Lys | Leu | Glu | Gly |
| 150 | His | Trp | Thr | Gln | Lys | Leu | Asp | Asp |
| 151 | His | Trp | Thr | Gln | Thr | Pro | Glu | Gly |
| 152 | His | Trp | Thr | Gln | Thr | Pro | Asp | Asp |
| 153 | His | Trp | Thr | Gln | Thr | Leu | Glu | Asp |
| 154 | His | Trp | Thr | Glu | Lys | Pro | Glu | Gly |
| 155 | His | Trp | Thr | Glu | Lys | Pro | Asp | Asp |
| 156 | His | Trp | Thr | Glu | Lys | Leu | Glu | Asp |
| 157 | His | Trp | Thr | Glu | Thr | Pro | Glu | Asp |
| 158 | His | Trp | Ala | Gln | Lys | Pro | Glu | Gly |
| 159 | His | Trp | Ala | Gln | Lys | Pro | Asp | Asp |
| 160 | His | Trp | Ala | Gln | Lys | Leu | Glu | Asp |
| 161 | His | Trp | Ala | Gln | Thr | Pro | Glu | Asp |
| 162 | His | Trp | Ala | Glu | Lys | Pro | Glu | Asp |
| 163 | His | Trp | Ala | Gln | Lys | Pro | Glu | Asp |
| 164 | His | Trp | Thr | Glu | Lys | Pro | Glu | Asp |
| 165 | His | Trp | Thr | Gln | Thr | Pro | Glu | Asp |
| 166 | His | Trp | Thr | Gln | Lys | Leu | Glu | Asp |
| 167 | His | Trp | Thr | Gln | Lys | Pro | Asp | Asp |
| 168 | His | Trp | Thr | Gln | Lys | Pro | Glu | Gly |
| 169 | His | Gln | Ala | Glu | Lys | Pro | Glu | Asp |
| 170 | His | Gln | Ala | Gln | Thr | Pro | Glu | Asp |
| 171 | His | Gln | Ala | Gln | Lys | Leu | Glu | Asp |
| 172 | His | Gln | Ala | Gln | Lys | Pro | Asp | Asp |
| 173 | His | Gln | Ala | Gln | Lys | Pro | Glu | Gly |
| 174 | His | Gln | Thr | Glu | Thr | Pro | Glu | Asp |
| 175 | His | Gln | Thr | Glu | Lys | Leu | Glu | Asp |
| 176 | His | Gln | Thr | Glu | Lys | Pro | Asp | Asp |
| 177 | His | Gln | Thr | Glu | Lys | Pro | Glu | Gly |
| 178 | His | Gln | Thr | Gln | Thr | Leu | Glu | Asp |
| 179 | His | Gln | Thr | Gln | Thr | Pro | Asp | Asp |
| 180 | His | Gln | Thr | Gln | Thr | Pro | Glu | Gly |
| 181 | His | Gln | Thr | Gln | Lys | Leu | Asp | Asp |
| 182 | His | Gln | Thr | Gln | Lys | Leu | Glu | Gly |
| 183 | His | Gln | Thr | Gln | Lys | Pro | Asp | Gly |
| 184 | Ser | Trp | Ala | Glu | Lys | Pro | Glu | Asp |
| 185 | Ser | Trp | Ala | Gln | Thr | Pro | Glu | Asp |
| 186 | Ser | Trp | Ala | Gln | Lys | Leu | Glu | Asp |
| 187 | Ser | Trp | Ala | Gln | Lys | Pro | Asp | Asp |
| 188 | Ser | Trp | Ala | Gln | Lys | Pro | Glu | Gly |
| 189 | Ser | Trp | Thr | Glu | Thr | Pro | Glu | Asp |
| 190 | Ser | Trp | Thr | Glu | Lys | Leu | Glu | Asp |
| 191 | Ser | Trp | Thr | Glu | Lys | Pro | Asp | Asp |
| 192 | Ser | Trp | Thr | Glu | Lys | Pro | Glu | Gly |
| 193 | Ser | Trp | Thr | Gln | Thr | Leu | Glu | Asp |
| 194 | Ser | Trp | Thr | Gln | Thr | Pro | Asp | Asp |
| 195 | Ser | Trp | Thr | Gln | Thr | Pro | Glu | Gly |
| 196 | Ser | Trp | Thr | Gln | Lys | Leu | Asp | Asp |
| 197 | Ser | Trp | Thr | Gln | Lys | Leu | Glu | Gly |
| 198 | Ser | Trp | Thr | Gln | Lys | Pro | Asp | Gly |
| 199 | Ser | Gln | Ala | Glu | Thr | Pro | Glu | Asp |
| 200 | Ser | Gln | Ala | Glu | Lys | Leu | Glu | Asp |
| 201 | Ser | Gln | Ala | Glu | Lys | Pro | Asp | Asp |
| 202 | Ser | Gln | Ala | Glu | Lys | Pro | Glu | Gly |
| 203 | Ser | Gln | Ala | Gln | Thr | Leu | Glu | Asp |
| 204 | Ser | Gln | Ala | Gln | Thr | Pro | Asp | Asp |
| 205 | Ser | Gln | Ala | Gln | Thr | Pro | Glu | Gly |
| 206 | Ser | Gln | Ala | Gln | Lys | Leu | Asp | Asp |
| 207 | Ser | Gln | Ala | Gln | Lys | Leu | Glu | Gly |
| 208 | Ser | Gln | Ala | Gln | Lys | Pro | Asp | Gly |
| 209 | Ser | Gln | Thr | Glu | Thr | Leu | Glu | Asp |
| 210 | Ser | Gln | Thr | Glu | Thr | Pro | Asp | Asp |
| 211 | Ser | Gln | Thr | Glu | Thr | Pro | Glu | Gly |
| 212 | Ser | Gln | Thr | Glu | Lys | Leu | Asp | Asp |
| 213 | Ser | Gln | Thr | Glu | Lys | Leu | Glu | Gly |
| 214 | Ser | Gln | Thr | Glu | Lys | Pro | Asp | Gly |
| 215 | Ser | Gln | Thr | Gln | Thr | Leu | Asp | Asp |
| 216 | Ser | Gln | Thr | Gln | Thr | Leu | Glu | Gly |
| 217 | Ser | Gln | Thr | Gln | Thr | Pro | Asp | Gly |
| 218 | Ser | Gln | Thr | Gln | Lys | Leu | Asp | Gly |
| 219 | His | Trp | Thr | Gln | Lys | Pro | Glu | Asp |
| 220 | His | Gln | Ala | Gln | Lys | Pro | Glu | Asp |
| 221 | His | Gln | Thr | Glu | Lys | Pro | Glu | Asp |
| 222 | His | Gln | Thr | Gln | Thr | Pro | Glu | Asp |
| 223 | His | Gln | Thr | Gln | Lys | Leu | Glu | Asp |
| 224 | His | Gln | Thr | Gln | Lys | Pro | Asp | Asp |
| 225 | His | Gln | Thr | Gln | Lys | Pro | Glu | Gly |
| 226 | Ser | Trp | Ala | Gln | Lys | Pro | Glu | Asp |
| 227 | Ser | Trp | Thr | Glu | Lys | Pro | Glu | Asp |
| 228 | Ser | Trp | Thr | Gln | Thr | Pro | Glu | Asp |
| 229 | Ser | Trp | Thr | Gln | Lys | Leu | Glu | Asp |
| 230 | Ser | Trp | Thr | Gln | Lys | Pro | Asp | Asp |
| 231 | Ser | Trp | Thr | Gln | Lys | Pro | Glu | Gly |
| 232 | Ser | Gln | Ala | Glu | Lys | Pro | Glu | Asp |
| 233 | Ser | Gln | Ala | Gln | Thr | Pro | Glu | Asp |
| 234 | Ser | Gln | Ala | Gln | Lys | Leu | Glu | Asp |
| 235 | Ser | Gln | Ala | Gln | Lys | Pro | Asp | Asp |
| 236 | Ser | Gln | Ala | Gln | Lys | Pro | Glu | Gly |
| 237 | Ser | Gln | Thr | Glu | Thr | Pro | Glu | Asp |
| 238 | Ser | Gln | Thr | Glu | Lys | Leu | Glu | Asp |
| 239 | Ser | Gln | Thr | Glu | Lys | Pro | Asp | Asp |
| 240 | Ser | Gln | Thr | Glu | Lys | Pro | Glu | Gly |
| 241 | Ser | Gln | Thr | Gln | Thr | Leu | Glu | Asp |
| 242 | Ser | Gln | Thr | Gln | Thr | Pro | Asp | Asp |
| 243 | Ser | Gln | Thr | Gln | Thr | Pro | Glu | Gly |
| 244 | Ser | Gln | Thr | Gln | Lys | Leu | Asp | Asp |
| 245 | Ser | Gln | Thr | Gln | Lys | Leu | Glu | Gly |
| 246 | Ser | Gln | Thr | Gln | Lys | Pro | Asp | Gly |
| 247 | His | Gln | Thr | Gln | Lys | Pro | Glu | Asp |
| 248 | Ser | Trp | Thr | Gln | Lys | Pro | Glu | Asp |

TABLE I-continued

| | Amino Acid Position | | | | | | | |
|---|---|---|---|---|---|---|---|---|
| Compound | 97 | 100 | 101 | 105 | 106 | 107 | 108 | 111 |
| 249 | Ser | Gln | Ala | Gln | Lys | Pro | Glu | Asp |
| 250 | Ser | Gln | Thr | Glu | Lys | Pro | Glu | Asp |
| 251 | Ser | Gln | Thr | Gln | Thr | Pro | Glu | Asp |
| 252 | Ser | Gln | Thr | Gln | Lys | Leu | Glu | Asp |
| 253 | Ser | Gln | Thr | Gln | Lys | Pro | Asp | Asp |
| 254 | Ser | Gln | Thr | Gln | Lys | Pro | Glu | Gly |
| 255 | Ser | Gln | Thr | Gln | Lys | Pro | Glu | Asp |

Other preferred proteins are those wherein Xaa at position 27 is Ala; Xaa at position 77 is Ser; Xaa at position 118 is Gly; and the amino residues at positions 97, 100, 101, 105, 106, 107, 108 and 111 are as described in Table I.

Experiments leading to the present invention were performed with five to six month old male, inbred normal ICR mice, inbred normal(ob/+), obese-diabetic mice (ob/ob) from the Jackson Laboratories (Bar Harbor, Maine) or Harlan (England), and obese-diabetic (db/db) mice.

Both normal and diabetic mice were housed three or six per plastic cage (with bedding) and water and feed were available ad libitum. The temperature of animal rooms was maintained at 23°±2°C. and lights were on from 0600 to 1800 h. Blood samples were collected from the tail vein. The most closely related biological test is, therefore, to inject the test article by any of several routes of administration (e.g., i.v., s.c., i.p., or by minipump or cannula) and then to monitor food and water consumption, body weight gain, plasma chemistry or hormones (glucose, insulin, ACTH, corticosterone, GH, T4) over various time periods. Suitable test animals include normal mice (ICR, etc.) and obese mice (ob/ob, Avy/a, KK-Ay, tubby, fat). Controls for nonspecific effects for these injections can be done using vehicle with or without test articles of similar composition in the same animal monitoring the same parameters or the test article itself in animals that are thought to lack the receptor (db/db mice, fa/fa or cp/cp rats).

Blood glucose levels were measured by a glucose oxidase method or a coupled hexokinase method. Plasma insulin was determined with radioimmunoassay kits using rat insulin as the standard. Plasma triglycerides were measured using commercial kits with glycerol as the standard.

The foregoing studies demonstrated that leptin and leptin mimetics, regulated food intake and body weight in normal ICR and genetically obese ob/ob mice. Chronic administration of leptin and leptin mimetics to ob/ob mice totally ameliorated the diabetic state of these animals showing the potential promise for these anti-diabetic proteins as a treatment for obese type II diabetics.

The compounds useful for carring out the present invention may be produced by well known chemical procedures, such as solution or solid-phase peptide synthesis, or semi-synthesis in solution beginning with protein fragments coupled through conventional solution methods. Such methods are well known in the art and may be found in general texts in the area such as H. Dugas and C. Penney, BIOORGANIC CHEMISTRY, (1981) at pages 54–92.

For example, peptides may be synthesized by solid-phase methodology utilizing an PE-Applied Biosystems 430A peptide synthesizer (commercially available from Applied Biosystems, Foster City Calif.) and synthesis cycles supplied by Applied Biosystems. t-Butoxycarbonyl (Boc)- protected amino acids and other reagents are commercially available from chemical supply houses. Sequential Boc chemistry using double couple protocols are applied to the starting p-methyl benzhydryl amine resins for the production of C-terminal carboxamides. For the production of C-terminal acids, the corresponding PAM resin is used. Arginine, Asparagine, Glutamine, Histidine and Methionine are coupled using preformed hydroxy benzotriazole esters. The following side chain protection may be used:

Arg, Tosyl
Asp, cyclohexyl or benzyl
Cys, 4-methylbenzyl
Glu, cyclohexyl
His, benzyloxymethyl
Lys, 2-chlorobenzyloxycarbonyl
Met, sulfoxide
Ser, Benzyl
Thr, Benzyl
Trp, formyl
Tyr, 4-bromo carbobenzoxy Boc deprotection may be accomplished with trifluoroacetic acid (TFA) in methylene chloride. Formyl removal from Trp is accomplished by treatment of the peptidyl resin with 20% piperidine in dimethylformamide for 60 minutes at 4° C. Met(O) can be reduced by treatment of the peptidyl resin with TFA/dimethylsulfide/concHCl (95/5/1) at 25° C. for 60 minutes. Following the above pre-treatments, the peptides may be further deprotected and cleaved from the resin with anhydrous hydrogen fluoride containing a mixture of 10% m-cresol or m-cresol/10% p-thiocresol or m-cresol/p-thiocresol/dimethyl-sulfide. Cleavage of the side chain protecting group(s) and of the peptide from the resin is carried out at zero degrees Centigrade or below, preferably –20° C. for thirty minutes followed by thirty minutes at 0° C. After removal of the HF, the peptide/resin is washed with ether. The peptide is extracted with glacial acetic acid and lyophilized. Purification is accomplished by reverse-phase C18 chromatography (Vydac) column in 0.1% TFA with a gradient of increasing acetonitrile concentration.

One skilled in the art recognizes that the solid phase synthesis could also be accomplished using the FMOC strategy and a TFA/scavenger cleavage mixture.

Proteins useful in the presently claimed methods also may be prepared by well known recombinant DNA techniques such as those described in Maniatis, et al. (1988) *Molecular Cloning: A Laboratory Manual*, Cold Spring Harbor Press, Cold Spring Harbor Laboratory, Cold Spring Harbor, New York or *Current Protocols in Molecular Biology* (1989) and supplements. Techniques for making substitutional mutations at predetermined sites in DNA having a known sequence are well known, for example M13 primer mutagenesis. The mutations that might be made in the DNA encoding the present anti-diabetic proteins must not place the sequence out of reading frame and preferably will not create complementary regions that could produce secondary mRNA structure See, DeBoer, et al., European Patent Publication, 075,444 A (1983).

Recombinant methods are generally preferred if larger quantities are desired. The basic steps in the recombinant production of protein include:

a) construction of a synthetic or semi-synthetic (or isolation from natural sources) DNA encoding the desired protein, b) integrating the coding sequence into an expression vector in a manner suitable for the expression of the protein either alone or as a fusion protein, c) transforming an appropriate eukaryotic or prokaryotic host cell with the expression vector, and d) recovering and purifying the recombinantly produced protein.

a. Gene Construction

Synthetic genes, the in vitro or in vivo transcription and translation of which will result in the production of the protein may be constructed by techniques well known in the art. Owing to the natural degeneracy of the genetic code, the skilled artisan will recognize that a sizable yet definite number of DNA sequences may be constructed which encode the desired proteins. In the preferred practice of the invention, synthesis is achieved by recombinant DNA technology.

Methodology of synthetic gene construction is well known in the art. For example, see Brown, et al. (1979) Methods in Enzymology, Academic Press, N.Y., Vol. 68, pgs. 109–151. The DNA sequence coding for the desired protein may be generated using conventional DNA synthesizing apparatus such as the Applied Biosystems Model 380A or 380B DNA synthesizers (commercially available from Applied Biosystems, Inc., 850 Lincoln Center Drive, Foster City, Calif. 94404).

It may desirable in some applications to modify the coding sequence of the desired protein so as to incorporate a convenient protease sensitive cleavage site, e.g., between the signal peptide and the structural protein facilitating the controlled excision of the signal peptide from the fusion protein construct.

DNA encoding the desired protein may also be created by using polymerase chain reaction (PCR) techniques. The template can be a cDNA library (commercially available from CLONETECH or STRATAGENE) or mRNA isolated from human adipose tissue. Such methodologies are well known in the art Maniatis, et al., Supra.

b. Direct Expression or Fusion Protein

The desired protein may be made either by direct expression or as fusion protein comprising the desired protein followed by enzymatic or chemical cleavage. A variety of peptidases (e.g. trypsin) which cleave a polypeptide at specific sites or digest the peptides from the amino or carboxy termini (e.g. diaminopeptidase) of the peptide chain are known. Furthermore, particular chemicals (e.g. cyanogen bromide) will cleave a polypeptide chain at specific sites. The skilled artisan will appreciate the modifications necessary to the amino acid sequence (and synthetic or semi-synthetic coding sequence if recombinant means are employed) to incorporate site-specific internal cleavage sites. See e.g., P. Carter, "Site Specific Proteolysis of Fusion Proteins", Ch. 13 in PROTEIN PURIFICATION: FROM MOLECULAR MECHANISMS TO LARGE SCALE PROCESSES, American Chemical Society, Washington, D.C. (1990).

c. Vector Construction

Construction of suitable vectors containing the desired coding and control sequences employ standard ligation techniques. Isolated plasmids or DNA fragments are cleaved, tailored, and religated in the form desired to form the plasmids required.

To effect the translation of the desired protein, one inserts the engineered synthetic DNA sequence in any of a plethora of appropriate recombinant DNA expression vectors through the use of appropriate restriction endonucleases. A synthetic coding sequence can be designed to possess restriction endonuclease cleavage sites at either end of the transcript to facilitate isolation from and integration into these expression and amplification and expression plasmids. The isolated cDNA coding sequence may be readily modified by the use of synthetic linkers to facilitate the incorporation of this sequence into the desired cloning vectors by techniques well known in the art. The particular endonucleases employed will be dictated by the restriction endonuclease cleavage pattern of the parent expression vector to be employed. The choice of restriction sites are chosen so as to properly orient the coding sequence with control sequences to achieve proper in-frame reading and expression of the desired protein.

In general, plasmid vectors containing promoters and control sequences which are derived from species compatible with the host cell are used with these hosts. The vector ordinarily carries a replication site as well as marker sequences which are capable of providing phenotypic selection in transformed cells. For example, E. coli is typically transformed using pBR322, a plasmid derived from an E. coli species (Bolivar, et al., Gene 2: 95 (1977)). Plasmid pBR322 contains genes for ampicillin and tetracycline resistance and thus provides easy means for identifying transformed cells. The pBR322 plasmid, or other microbial plasmid must also contain or be modified to contain promoters and other control elements commonly used in recombinant DNA technology.

The desired coding sequence is inserted into an expression vector in the proper orientation to be transcribed from a promoter and ribosome binding site, both of which should be functional in the host cell in which the protein is to be expressed. An example of such an expression vector is a plasmid described in Belagaje et al., U.S. Pat. No. 5,304,493, the teachings of which are herein incorporated by reference. The gene encoding A-C-B proinsulin described in U.S. Pat. No. 5,304,493 can be removed from the plasmid pRB182 with restriction enzymes NdeI and BmHI. The genes encoding the protein of the present invention can be inserted into the plasmid backbone on a NdeI/BamHI restriction fragment cassette.

d. Prokaryotic expression

In general, prokaryotes are used for cloning of DNA sequences in constructing the vectors useful in the invention. For example, E. coli K12 strain 294 (ATCC No. 31446) is particularly useful. Other microbial strains which may be used include E. coli B and E. coli X1776 (ATCC No. 31537). These examples are illustrative rather than limiting.

Prokaryotes also are used for expression. The aforementioned strains, as well as E. coli W3110 (prototrophic, ATCC No. 27325), bacilli such as Bacillus subtilis, and other enterobacteriaceae such as Salmonella typhimurium or Serratia marcescans, and various pseudomonas species may be used. Promoters suitable for use with prokaryotic hosts include the β-lactamase (vector pGX2907 [ATCC 39344] contains the replicon and β-lactamase gene) and lactose promoter systems (Chang et al., Nature, 275:615 (1978); and Goeddel et al., Nature 281:544 (1979)), alkaline phosphatase, the tryptophan (trp) promoter system (vector PATH1 [ATCC 37695] is designed to facilitate expression of an open reading frame as a trpE fusion protein under control of the trp promoter) and hybrid promoters such as the tac promoter (isolatable from plasmid pDR540 ATCC-37282). However, other functional bacterial promoters, whose nucleotide sequences are generally known, enable one of skill in the art to ligate them to DNA encoding the protein using linkers or adaptors to supply any required restriction sites. Promoters for use in bacterial systems also will contain a Shine-Dalgarno sequence operably linked to the DNA encoding protein.

e. Eukaryotic expression

The protein may be recombinantly produced in eukaryotic expression systems. Preferred promoters controlling transcription in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. β-actin promoter. The early and late promoters of the SV40 virus are conveniently obtained as an SV40 restriction fragment which also contains the SV40 viral origin of replication. Fiers, et al., *Nature*, 273:113 (1978). The entire SV40 genome may be obtained from plasmid PBRSV, ATCC 45019. The immediate early promoter of the human cytomegalovirus may be obtained from plasmid pCMBβ (ATCC 77177). Of course, promoters from the host cell or related species also are useful herein.

Transcription of a DNA encoding the desired protein by higher eukaryotes is increased by inserting an enhancer sequence into the vector. Enhancers are cis-acting elements of DNA, usually about 10–300 bp, that act on a promoter to increase its transcription. Enhancers are relatively orientation and position independent having been found 5' (Laimins, L. et al., *PNAS* 78: 993 (1981)) and 3' (Lusky, M. L., et al., *Mol. Cell Bio.* 3: 1108 (1983)) to the transcription unit, within an intron (Banerji, J. L. et al., *Cell* 33: 729 (1983)) as well as within the coding sequence itself (Osborne, T. F., et al., *Mol. Cell Bio.* 4: 1293 (1984)). Many enhancer sequences are now known from mammalian genes (globin, RSV, SV40, EMC, elastase, albumin, a-fetoprotein and insulin). Typically, however, one will use an enhancer from a eukaryotic cell virus. Examples include the SV40 late enhancer, the cytomegalovirus early promoter enhancer, the polyoma enhancer on the late side of the replication origin, and adenovirus enhancers.

Expression vectors used in eukaryotic host cells (yeast, fungi, insect, plant, animal, human or nucleated cells from other multicellular organisms) will also contain sequences necessary for the termination of transcription which may affect mRNA expression. These regions are transcribed as polyadenylated segments in the untranslated portion of the mRNA encoding protein. The 3' untranslated regions also include transcription termination sites.

Expression vectors may contain a selection gene, also termed a selectable marker. Examples of suitable selectable markers for mammalian cells are dihydrofolate reductase (DHFR, which may be derived from the BglII/HindIII restriction fragment of pJOD-10 [ATCC 68815]), thymidine kinase (herpes simplex virus thymidine kinase is contained on the BmHI fragment of vP-5 clone [ATCC 2028]) or neomycin (G418) resistance genes (obtainable from pNN414 yeast artificial chromosome vector [ATCC 37682]). When such selectable markers are successfully transferred into a mammalian host cell, the transfected mammalian host cell can survive if placed under selective pressure. There are two widely used distinct categories of selective regimes. The first category is based on a cell's metabolism and the use of a mutant cell line which lacks the ability to grow without a supplemented media. Two examples are: CHO DHFR⁻cells (ATCC CRL-9096) and mouse LTK–cells (L-M(TK-) ATCC CCL-2.3). These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in nonsupplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, Southern P. and Berg, P., *J. Molec. Appl. Genet.* 1: 327 (1982), mycophenolic acid, Mulligan, R. C. and Berg, P. *Science* 209: 1422 (1980), or hygromycin, Sugden, B. et al., *Mol Cell. Biol.* 5: 410–413 (1985). The three examples given above employ bacterial genes under eukaryotic control to convey resistance to the appropriate drug G418 or neomycin (geneticin), xgpt (mycophenolic acid) or hygromycin, respectively.

A preferred vector for eukaryotic expression is pRc/CMV. pRc/CMV is commercially available from Invitrogen Corporation, 3985 Sorrento Valley Blvd., San Diego, Calif. 92121. To confirm correct sequences in plasmids constructed, the ligation mixtures are used to transform *E. coli* K12 strain DH5a (ATCC 31446) and successful transformants selected by antibiotic resistance where appropriate. Plasmids from the transformants are prepared, analyzed by restriction and/or sequence by the method of Messing, et al., *Nucleic Acids Res.* 9:309 (1981).

Host cells may be transformed with the expression vectors of this invention and cultured in conventional nutrient media modified as is appropriate for inducing promoters, selecting transformants or amplifying genes. The culture conditions, such as temperature, pH and the like, are those previously used with the host cell selected for expression, and will be apparent to the ordinarily skilled artisan. The techniques of transforming cells with the aforementioned vectors are well known in the art and may be found in such general references as Maniatis, et al., *Molecular Cloning: A Laboratory Manual*, Cold Spring Harbor Press, Cold Spring Harbor Laboratory, Cold Spring Harbor, New York (1989), or *Current Protocols in Molecular Biology* (1989) and supplements.

Preferred suitable host cells for expressing the vectors encoding the desired proteins in higher eukaryotes include: African green monkey kidney line cell line transformed by SV40 (COS-7, ATCC CRL-1651); transformed 10 human primary embryonal kidney cell line 293,(Graham, F. L. et al., *J. Gen Virol.* 6: 59–72 (1977), *Virology* 77: 319–329, Virology 86: 10–21); baby hamster kidney cells (BHK-21(C-13), ATCC CCL-10, *Virology* 16: 147 (1962)); chinese hamster ovary cells CHO-DHFR⁻(ATCC CRL-9096), mouse Sertoli cells (TM4, ATCC CRL-1715, *Biol. Reprod.* 23: 243–250 (1980)); african green monkey kidney cells (VERO 76, ATCC CRL-1587); human cervical epitheloid carcinoma cells (HeLa, ATCC CCL-2); canine kidney cells (MDCK, ATCC CCL-34); buffalo rat liver cells (BRL 3A, ATCC CRL-1442); human diploid lung cells (WI-38, ATCC CCL-75); human hepatocellular carcinoma cells (Hep G2, ATCC HB-8065);and mouse mammary tumor cells (MMT 060562, ATCC CCL51).

f. Yeast expression

In addition to prokaryotes, eukaryotic microbes such as yeast cultures may also be used. Saccharomyces cerevisiae, or common baker's yeast is the most commonly used eukaryotic microorganism, although a number of other strains are commonly available. For expression in Saccharomyces, the plasmid YRp7, for example, (ATCC-40053, Stinchcomb, et al., *Nature* 282: 39 (1979); Kingsman et al., *Gene* 7: 141 (1979); Tschemper et al., *Gene* 10: 157 (1980)) is commonly used. This plasmid already contains the trp gene which provides a selection marker for a mutant strain of yeast lacking the ability to grow in tryptophan, for example ATCC no. 44076 or PEP4-1 (Jones, *Genetics* 85: 12 (1977)).

Suitable promoting sequences for use with yeast hosts include the promoters for 3-phosphoglycerate kinase (found on plasmid pAP12BD ATCC 53231 and described in U.S. Pat. No. 4,935,350, Jun. 19, 1990) or other glycolytic enzymes such as enolase (found on plasmid pAC1 ATCC 39532), glyceraldehyde-3-phosphate dehydrogenase (derived from plasmid pHcGAPC1 ATCC 57090, 57091), zymomonas mobilis (U.S. Pat. No. 5,000,000 issued Mar. 19, 1991), hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein (contained on plasmid vector pCL28XhoLHBPV ATCC 39475, U.S. Pat. No. 4,840,896), glyceraldehyde 3-phosphate dehydrogenase, and enzymes responsible for maltose and galactose (GAL1 found on plasmid pRY121 ATCC 37658) utilization. Suitable vectors and promoters for use in yeast expression are further described in R. Hitzeman et al., European Patent Publication No. 73,657A. Yeast enhancers such as the UAS Gal from Saccharomyces cerevisiae (found in conjunction with the CYC1 promoter on plasmid YEpsec—hIIbeta ATCC 67024), also are advantageously used with yeast promoters.

The present invention provides a method for treating obese type II diabetics. The method comprises administering an effective amount of a leptin or leptin mimetic in a dose between about 1 and 10,000 μg/kg. A preferred dose is from about 20 to 1,000 μg/kg. A more preferred dose is from about 50 to 500 μg/kg. A typical daily dose for an adult human is from about 0.5 to 100 mg. In practicing this method, anti-diabetic proteins can be administered in a single daily dose or in multiple doses per day. The treatment regime may require administration over extended periods of time. The amount per administered dose or the total amount administered will be determined by the physician and depend on such factors as the mass of the patient, the age and general health of the patient and the tolerance of the patient to the compound.

In the practice of the present invention, it is useful, but not essential to prepare pharmaceutical formulations comprising anti-diabetic proteins. Such proteins, preferably in the form of a pharmaceutically acceptable salt, can be formulated for parenteral administration. For example, compounds can be admixed with conventional pharmaceutical carriers and excipients. The compositions comprising desired proteins contain from about 0.1 to 90% by weight of the active protein, preferably in a soluble form, and more generally from about 0.1 to 1.0%. Furthermore, the present proteins may be administered alone or in combination with other anti-obesity agents or agents useful in treating diabetes.

For intravenous use, the protein is administered in commonly used intravenous fluids and administered by infusion. For intramuscular preparations, a sterile formulation, preferably a suitable soluble salt form of the protein, for example the hydrochloride salt, can be dissolved and administered in a pharmaceutical diluent such as pyrogen-free water or physiological saline. A suitable insoluble form of the compound may be prepared and administered as a suspension in an aqueous base or a pharmaceutically acceptable oil base, e.g. an ester of a long chain fatty acid such as ethyl oleate.

In a preferred embodiment, the present invention provides a method for treating obese type II diabetics with low leptin levels, though diabetic patients with high endogenous leptin levels may also benefit from the presently claimed methods. Methods for assaying serum and plasma leptin levels may be accomplished using standard antibody-based methodologies. Leptin assay kits are also commercially available from Linco Research, Inc. (14 Research Park Dr., St Louis, Mo. 63304)

Treating obese type II diabetics having leptin levels between 0 and 80 ng/ml is preferred. More preferred is to treat obese type II diabetics having leptin levels between 0 and 50 ng/ml. More highly preferred is to treat obese type II diabetics having leptin levels between 0 and 30 ng/ml. Most preferred is to treat obese type II diabetics having leptin levels between 0 and 15 ng/ml.

By way of illustration, the following examples are provided to help describe how to make and practice the various embodiments of the invention. These example are in no way meant to limit the scope of the invention.

EXAMPLE 1

A DNA sequence encoding the following protein sequence:

Met-Arg-SEQ ID NO:4.

was obtained using standard PCR methodology from a human fat cell library (commercially available from CLONETECH). Briefly, degenerate primers were designed based on the published amino acid sequence of the human ob gene. The primers were prepared for use in polymerase chain reaction (PCR) amplification methods using a Model 380A DNA synthesizers (PE-Applied Biosystems, Inc., 850 Lincoln Center Drive, Foster City, CA 94404). Forward primers OB.F1M (5-GG GG CAT ATG AGG GTA CCT ATC CAG AAA GTC CAG GAT GAC AC)and OB.F2H (5-GG GG CAT ATG AGG GTA CCC ATC CAG AAG GTG CAG GAC GA)(and reverse primers OB.R1M (5-GG GG GGATC GAT AAT TTA GCA TCC AGG GCT AAG ATC CAA CTG CCA AAG CAT) and OB.R2H (5-GG GG GGATC CTA TTA GCA CCC GGG AGA CAG GTC CAG CTG CCA CAA CAT) were mixed together with a PCR-ready human fat cell CDNA as the template (Clontech Laboratories, Inc., 4030 Fabian Way, Palo Alto, Calif. 94303; Item #7128-1).

The 2 sets of PCR amplifications were performed using 2.5 units of Amplitag DNA polymerase (Perkin Elmer Cetus) or 2 units of Vent DNA polymerase (New England Biolabs) in 100 uL reactions. PCR reactions contained 1 uL of human fat cell cDNA, 10 pmol of each primer (all four were mixed). The following conditions were used for "Touchdown PCR": 2 cycles: 94° C.×30 sec, 60° C.×30 sec, 72° C.×45 sec 2 cycles: 94° C.×30 sec, 56° C. ×30 sec, 72° C.×45 sec; 2cycles: 94° C.×30 sec. 52° C.×30 sec, 72C.×45 sec; 2cycles: 94° C.×30 sec, 48° C.×30 sec, 72C.×45 sec; 2 cycles: 94° C.×30 sec, 44° C.×30 sec, 72° C.×45 sec: 28 cycles 94° C.×30 sec, 52° C.×30 sec, 72° C.×45 sec The resultant PCR reactions products were run on a 1% agarose gel and a band of an approximate 450 bp in size was visualized by ethidium bromide staining. This band was present in both sets of PCR reactions. The bands 20 were excised and reamplified using above conditions in 30 cycles (94×30 sec, 52×30, 72×45). The PCR product obtained using Vent DNA polymerase was gel purified and cloned into a pCR-SCRIPT cloning vector (Stratagene). The vector was then used to transform *E. coli* cells. Plasmid DNA was isolated from 20 white colonies of *E. coli* and samples from three clones were sequenced. Two such colonies, *E. coli* DH10B/pOJ717 and *E. coli* DH10B/pOJ718 were deposited with the Northern Regional Research Laboratories (NRRL) under terms of the Budapest Treaty and are available under Accession Numbers B-21408 and B-21409 respectively.

EXAMPLE 2

Vector Construction

A plasmid containing the DNA sequence encoding a desired protein is constructed to include NdeI and BamHI restriction sites. The plasmid carrying the cloned PCR product is digested with NdeI and BamHI restriction enzymes. The small~450bp fragment is gel-purified and ligated into the vector pRB182 from which the coding sequence for A-C-B proinsulin is deleted. The ligation products are transformed into *E. coli* DH10B (commercially available) and colonies growing on tryptone-yeast plates supplemented with 10 µg/mL of tetracycline are analyzed. Plasmid DNA is isolated, digested with NdeI and BamHI and the resulting fragments are separated by agarose gel electrophoresis. Plasmids containing the expected~450bp NdeI to BamHI fragment are kept. *E. coli* B BL21 (DE3) are transformed with this second plasmid expression suitable for culture for protein production.

The techniques of transforming cells with the aforementioned vectors are well known in the art and may be found in such general references as Maniatis, et al., MOLECULAR CLONING: A LABORATORY MANUAL, Cold Spring Harbor Press, Cold Spring Harbor Laboratory, Cold Spring Harbor, New York (1988), or CURRENT PROTOCOLS IN MOLECULAR BIOLOGY, (F. Ausabel, ed., 1989) and supplements thereof. The techniques involved in the transformation of *E. coli* cells used in the preferred practice of the invention as exemplified herein are well known in the art. The precise conditions under which the transformed *E. coli* cells are cultured is dependent on the nature of the *E. coli* host cell line and the expression or cloning vectors employed. For example, vectors which incorporate thermoinducible promoter-operator regions, such as the c1857 thermoinducible lambda-phage promoter-operator region, require a temperature shift from about 30° C. to about 40° C. in the culture conditions so as to induce protein synthesis.

In the preferred embodiment of the invention *E. coli* K12 RV308 cells are employed as host cells but numerous other cell lines are available such as, but not limited to, *E. coli* K12 L201, L687, L693, L507, L640, L641, L695, L814 (*E. coli* B). The transformed host cells are then plated on appropriate media under the selective pressure of the antibiotic corresponding to the resistance gene present on the expression plasmid. The cultures are then incubated for a time and temperature appropriate to the host cell line employed.

Proteins which are expressed in high-level bacterial expression systems characteristically aggregate in granules or inclusion bodies which contain high levels of the overexpressed protein. See, e.g., Kreuger et al., PROTEIN FOLDING, (Gierasch and King, eds., 1990) at pages 136–142, American Association for the Advancement of Science Publication No. 89-18S, Washington, D.C. Such protein aggregates must be solubilized to provide further purification and isolation of the desired protein product. Id. A variety of techniques using strongly denaturing solutions such as guanidinium-HCl and/or weakly denaturing solutions such as dithiothreitol (DTT) are used to solubilize the proteins.

Gradual removal of the denaturing agents (often by dialysis) in a solution allows the denatured protein to assume its native conformation. The particular conditions for denaturation and folding are determined by the particular protein expression system and/or the protein in question.

Preferably, the present proteins are expressed as Met-Arg-SEQ ID NO: X so that the expressed proteins may be readily converted to the desired protein with cathepsin C (also known as diaminopeptidase). The purification of proteins is by techniques known in the art and includes reverse phase chromatography, affinity chromatography, and size exclusion chromatography.

The desired proteins contain two cysteine residues. Thus, a di-sulfide bond may be formed to stabilize the protein. The present invention includes proteins wherein the Cys at position 96 is crosslinked to Cys at position 146 as well as those proteins without such di-sulfide bonds.

In addition the proteins useful in the present invention may exist, particularly when formulated, as dimers, trimers, tetramers, and other multimers. Such multimers are included within the scope of the present invention.

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 146 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:1:

```
Val  Pro  Ile  Gln  Lys  Val  Gln  Asp  Asp  Thr  Lys  Thr  Leu  Ile  Lys  Thr
 1             5                        10                           15

Ile  Val  Thr  Arg  Ile  Asn  Asp  Ile  Ser  His  Thr  Xaa  Ser  Val  Ser  Ser
                20                       25                       30
```

| | | | | | | | | | | | | | | |
|---|---|---|---|---|---|---|---|---|---|---|---|---|---|---|
| Lys | Gln | Lys<br>35 | Val | Thr | Gly | Leu | Asp<br>40 | Phe | Ile | Pro | Gly | Leu<br>45 | His | Pro | Ile |
| Leu | Thr<br>50 | Leu | Ser | Lys | Met | Asp<br>55 | Gln | Thr | Leu | Ala | Val<br>60 | Tyr | Gln | Gln | Ile |
| Leu<br>65 | Thr | Ser | Met | Pro | Ser<br>70 | Arg | Asn | Val | Ile | Gln<br>75 | Ile | Ser | Asn | Asp | Leu<br>80 |
| Glu | Asn | Leu | Arg | Asp<br>85 | Leu | Leu | His | Val | Leu<br>90 | Ala | Phe | Ser | Lys | Ser<br>95 | Cys |
| His | Leu | Pro | Gln<br>100 | Ala | Ser | Gly | Leu | Glu<br>105 | Thr | Leu | Glu | Ser | Leu<br>110 | Gly | Gly |
| Val | Leu | Glu<br>115 | Ala | Ser | Gly | Tyr | Ser<br>120 | Thr | Glu | Val | Val | Ala<br>125 | Leu | Ser | Arg |
| Leu | Gln | Gly<br>130 | Ser | Leu | Gln | Asp<br>135 | Met | Leu | Gln | Gln | Leu<br>140 | Asp | Leu | Ser | Pro |
| Gly | Cys<br>145 | | | | | | | | | | | | | | |

(2) INFORMATION FOR SEQ ID NO:2:

(i) SEQUENCE CHARACTERISTICS:
(A) LENGTH: 146 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:2:

| | | | | | | | | | | | | | | |
|---|---|---|---|---|---|---|---|---|---|---|---|---|---|---|
| Val<br>1 | Pro | Ile | Trp | Arg | Val<br>5 | Gln | Asp | Asp | Thr | Lys<br>10 | Thr | Leu | Ile | Lys | Thr |
| Ile | Val | Thr | Arg<br>20 | Ile | Ser | Asp | Ile | Ser<br>25 | His | Met | Gln | Ser | Val<br>30 | Ser | Ser |
| Lys | Gln | Arg<br>35 | Val | Thr | Gly | Leu | Asp<br>40 | Phe | Ile | Pro | Gly | Leu<br>45 | His | Pro | Val |
| Leu | Ser<br>50 | Leu | Ser | Lys | Met | Asp<br>55 | Gln | Thr | Leu | Ala | Ile<br>60 | Tyr | Gln | Gln | Ile |
| Leu<br>65 | Thr | Ser | Leu | Pro | Ser<br>70 | Arg | Asn | Val | Ile | Gln<br>75 | Ile | Ser | Asn | Asp | Leu<br>80 |
| Glu | Asn | Leu | Arg | Asp<br>85 | Leu | Leu | His | Leu | Leu<br>90 | Ala | Ser | Ser | Lys | Ser<br>95 | Cys |
| Pro | Leu | Pro | Gln<br>100 | Ala | Arg | Ala | Leu | Glu<br>105 | Thr | Leu | Glu | Ser | Leu<br>110 | Gly | Gly |
| Val | Leu | Glu<br>115 | Ala | Ser | Leu | Tyr | Ser<br>120 | Thr | Glu | Val | Val | Ala<br>125 | Leu | Ser | Arg |
| Leu | Gln<br>130 | Gly | Ala | Leu | Gln | Asp<br>135 | Met | Leu | Arg | Gln | Leu<br>140 | Asp | Leu | Ser | Pro |
| Gly | Cys<br>145 | | | | | | | | | | | | | | |

(2) INFORMATION FOR SEQ ID NO:3:

(i) SEQUENCE CHARACTERISTICS:
(A) LENGTH: 146 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:3:

```
Val  Pro  Ile  Cys  Lys  Val  Gln  Asp  Asp  Thr  Lys  Thr  Leu  Ile  Lys  Thr
 1              5                       10                        15

Ile  Val  Thr  Arg  Ile  Asn  Asp  Ile  Ser  His  Thr  Xaa  Ser  Val  Ser  Ser
              20                       25                        30

Lys  Gln  Arg  Val  Thr  Gly  Leu  Asp  Phe  Ile  Pro  Gly  Leu  His  Pro  Leu
         35                       40                       45

Leu  Ser  Leu  Ser  Lys  Met  Asp  Gln  Thr  Leu  Ala  Ile  Tyr  Gln  Gln  Ile
    50                       55                       60

Leu  Thr  Ser  Leu  Pro  Ser  Arg  Asn  Val  Val  Gln  Ile  Ser  Asn  Asp  Leu
65                       70                       75                        80

Glu  Asn  Leu  Arg  Asp  Leu  Leu  His  Leu  Leu  Ala  Ala  Ser  Lys  Ser  Cys
              85                       90                       95

Pro  Leu  Pro  Gln  Val  Arg  Ala  Leu  Glu  Ser  Leu  Glu  Ser  Leu  Gly  Val
              100                     105                      110

Val  Leu  Glu  Ala  Ser  Leu  Tyr  Ser  Thr  Glu  Val  Val  Ala  Leu  Ser  Arg
         115                      120                      125

Leu  Gln  Gly  Ser  Leu  Gln  Asp  Met  Leu  Arg  Gln  Leu  Asp  Leu  Ser  Pro
    130                      135                      140

Gly  Cys
145
```

( 2 ) INFORMATION FOR SEQ ID NO:4:

( i ) SEQUENCE CHARACTERISTICS:
        ( A ) LENGTH: 146 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:4:

```
Val  Pro  Ile  Gln  Lys  Val  Gln  Asp  Asp  Thr  Lys  Thr  Leu  Ile  Lys  Thr
 1              5                       10                        15

Ile  Val  Thr  Arg  Ile  Asn  Asp  Ile  Ser  His  Xaa  Xaa  Ser  Val  Ser  Ser
              20                       25                        30

Lys  Gln  Lys  Val  Thr  Gly  Leu  Asp  Phe  Ile  Pro  Gly  Leu  His  Pro  Ile
         35                       40                       45

Leu  Thr  Leu  Ser  Lys  Met  Asp  Gln  Thr  Leu  Ala  Val  Tyr  Gln  Gln  Ile
    50                       55                       60

Leu  Thr  Ser  Met  Pro  Ser  Arg  Asn  Val  Ile  Gln  Ile  Ser  Asn  Asp  Leu
65                       70                       75

Glu  Asn  Leu  Arg  Asp  Leu  Leu  His  Val  Leu  Ala  Phe  Ser  Lys  Ser  Cys
              85                       90                       95

His  Leu  Pro  Trp  Ala  Ser  Gly  Leu  Glu  Thr  Leu  Asp  Ser  Leu  Gly  Gly
              100                     105                      110

Val  Leu  Glu  Ala  Ser  Gly  Tyr  Ser  Thr  Glu  Val  Val  Ala  Leu  Ser  Arg
         115                      120                      125

Leu  Gln  Gly  Ser  Leu  Gln  Asp  Met  Leu  Trp  Gln  Leu  Asp  Leu  Ser  Pro
    130                      135                      140

Gly  Cys
145
```

( 2 ) INFORMATION FOR SEQ ID NO:5:

( i ) SEQUENCE CHARACTERISTICS:
        ( A ) LENGTH: 146 amino acids
        ( B ) TYPE: amino acid (C) STRANDEDNESS: single
(D) TOPOLOGY: linear (ii) MOLECULE TYPE: protein (xi) SEQUENCE DESCRIPTION: SEQ ID NO:5:

```
Val Pro Ile Gln Lys Val Gln Ser Asp Thr Lys Thr Leu Ile Lys Thr
1               5                   10                  15
Ile Val Thr Arg Ile Asn Asp Ile Ser His Thr Gln Ser Val Ser Ser
            20                  25                  30
Lys Gln Arg Val Thr Gly Leu Asp Phe Ile Pro Gly Leu His Pro Val
            35                  40                  45
Leu Thr Leu Ser Gln Met Asp Gln Thr Leu Ala Ile Tyr Gln Gln Ile
    50                  5                       60
Leu Ile Asn Leu Pro Ser Arg Asn Val Ile Gln Ile Ser Asn Asp Leu
65                  70                  75                  80
Glu Asn Leu Arg Asp Leu Leu His Leu Leu Ala Phe Ser Lys Ser Cys
                85                  90                  95
His Leu Pro Leu Ala Ser Gly Leu Glu Thr Leu Glu Ser Leu Gly Asp
            100                 105                 110
Val Leu Glu Ala Ser Leu Tyr Ser Thr Glu Val Val Ala Leu Ser Arg
            115                 120                 125
Leu Gln Gly Ser Leu Gln Asp Met Leu Trp Gln Leu Asp Leu Ser Pro
    130                 135                 140
Gly Cys
145
```

(2) INFORMATION FOR SEQ ID NO:6:

(i) SEQUENCE CHARACTERISTICS:
    (A) LENGTH: 146 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:6:

```
Val Pro Ile Gln Lys Val Gln Asp Asp Thr Lys Thr Leu Ile Lys Thr
1               5                   10                  15
Ile Val Thr Arg Ile Asn Asp Ile Ser His Thr Gln Ser Val Ser Ala
            20                  25                  30
Arg Gln Arg Val Thr Gly Leu Asp Phe Ile Pro Gly Leu His Pro Ile
            35                  40                  45
Leu Ser Leu Ser Lys Met Asp Gln Thr Leu Ala Val Tyr Gln Gln Ile
    50                  55                      60
Leu Thr Ser Leu Pro Ser Gln Asn Val Leu Gln Ile Ala His Asp Leu
65                  70                  75
Glu Asn Leu Arg Asp Leu Leu His Leu Leu Ala Phe Ser Lys Ser Cys
                85                  90                  95
Ser Leu Pro Gln Thr Arg Gly Leu Gln Lys Pro Glu Ser Leu Asp Gly
            100                 105                 110
Val Leu Glu Ala Ser Leu Tyr Ser Thr Glu Val Val Ala Leu Ser Arg
            115                 120                 125
Leu Gln Gly Ser Leu Gln Asp Ile Leu Gln Gln Leu Asp Leu Ser Pro
    130                 135                 140
Glu Cys
145
```

( 2 ) INFORMATION FOR SEQ ID NO:7:

( i ) SEQUENCE CHARACTERISTICS:
        ( A ) LENGTH: 146 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:7:

```
Val Pro Ile Gln Lys Val Gln Asp Asp Thr Lys Thr Leu Ile Lys Thr
 1               5                  10                  15

Ile Val Thr Arg Ile Xaa Asp Ile Ser His Xaa Xaa Ser Val Ser Ser
                20                  25                  30

Lys Gln Lys Val Thr Gly Leu Asp Phe Ile Pro Gly Leu His Pro Ile
            35                  40                  45

Leu Thr Leu Ser Lys Xaa Asp Gln Thr Leu Ala Val Tyr Gln Gln Ile
        50                  55                  60

Leu Thr Ser Xaa Pro Ser Arg Xaa Val Ile Gln Ile Xaa Asn Asp Leu
65                  70                  75                      80

Glu Asn Leu Arg Asp Leu Leu His Val Leu Ala Phe Ser Lys Ser Cys
                85                  90                      95

His Leu Pro Trp Ala Ser Gly Leu Glu Thr Leu Asp Ser Leu Gly Gly
            100                 105                 110

Val Leu Glu Ala Ser Xaa Tyr Ser Thr Glu Val Val Ala Leu Ser Arg
        115                 120                 125

Leu Gln Gly Ser Leu Gln Asp Met Leu Trp Gln Leu Asp Leu Ser Pro
    130                 135                 140

Gly Cys
145
```

( 2 ) INFORMATION FOR SEQ ID NO:8:

( i ) SEQUENCE CHARACTERISTICS:
        ( A ) LENGTH: 146 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:8:

```
Val Pro Ile Gln Lys Val Gln Asp Asp Thr Lys Thr Leu Ile Lys Thr
 1               5                  10                  15

Ile Val Thr Arg Ile Asn Asp Ile Ser His Xaa Gln Ser Val Ser Ser
                20                  25                  30

Lys Gln Lys Val Thr Gly Leu Asp Phe Ile Pro Gly Leu His Pro Ile
            35                  40                  45

Leu Thr Leu Ser Lys Met Asp Gln Thr Leu Ala Val Tyr Gln Gln Ile
        50                  55                  60

Leu Thr Ser Met Pro Ser Arg Asn Val Ile Gln Ile Xaa Asn Asp Leu
65                  70                  75                  80

Glu Asn Leu Arg Asp Leu Leu His Val Leu Ala Phe Ser Lys Ser Cys
                85                  90                  95

His Leu Pro Trp Ala Ser Gly Leu Glu Thr Leu Asp Ser Leu Gly Gly
            100                 105                 110

Val Leu Glu Ala Ser Xaa Tyr Ser Thr Glu Val Val Ala Leu Ser Arg
        115                 120                 125
```

```
Leu Gln Gly Ser Leu Gln Asp Met Leu Trp Gln Leu Asp Leu Ser Pro
    130             135             140
Gly Cys
145
```

(2) INFORMATION FOR SEQ ID NO:9:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

```
GGGGCATATG AGGGTACCTA TCCAGAAAGT CCAGGATGAC AC                42
```

(2) INFORMATION FOR SEQ ID NO:10:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

```
GGGGCATATG AGGGTACCCA TCCAGAAGGT GCAGGACGA                    39
```

(2) INFORMATION FOR SEQ ID NO:11:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

```
GGGGGGATCG ATAATTTAGC ATCCAGGGCT AAGATCCAAC TGCCAAAGCA T      51
```

(2) INFORMATION FOR SEQ ID NO:12:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

```
GGGGGGATCC TATTAGCACC CGGGAGACAG GTCCAGCTGC CACAACAT          48
```

I claim:

1. A method of treating or ameliorating diabetes mellitus, in a patient in need thereof, which comprises administering to an obese type II diabetic an effective amount of leptin, a leptin mimetic, or a pharmaceutically acceptable salt thereof.

2. A method of claim 1 wherein said leptin or leptin mimetic is selected from the group consisting of

```
    Val Pro Ile Gln Lys Val Gln Asp Asp Thr Lys Thr Leu Ile Lys Thr   (a)
     1           5                   10                  15
```

-continued

```
Ile  Val  Thr  Arg  Ile  Asn  Asp  Ile  Ser  His  Thr  Xaa  Ser  Val  Ser  Ser
               20                        25                       30
Lys  Gln  Lys  Val  Thr  Gly  Leu  Asp  Phe  Ile  Pro  Gly  Leu  His  Pro  Ile
          35                        40                       45
Leu  Thr  Leu  Ser  Lys  Met  Asp  Gln  Thr  Leu  Ala  Val  Tyr  Gln  Gln  Ile
     50                        55                       60
Leu  Thr  Ser  Met  Pro  Ser  Arg  Asn  Val  Ile  Gln  Ile  Ser  Asn  Asp  Leu
65                        70                       75                       80
Glu  Asn  Leu  Arg  Asp  Leu  Leu  His  Val  Leu  Ala  Phe  Ser  Lys  Ser  Cys
                    85                        90                       95
His  Leu  Pro  Gln  Ala  Ser  Gly  Leu  Glu  Thr  Leu  Glu  Ser  Leu  Gly  Gly
               100                       105                      110
Val  Leu  Glu  Ala  Ser  Gly  Tyr  Ser  Thr  Glu  Val  Val  Ala  Leu  Ser  Arg
          115                       120                      125
Leu  Gln  Gly  Ser  Leu  Gln  Asp  Met  Leu  Gln  Gln  Leu  Asp  Leu  Ser  Pro
     130                       135                      140
Gly  Cys
145
``` wherein: Xaa at position 28 is Gln or absent; (SEQ ID NO:1)

```
Val  Pro  Ile  Trp  Arg  Val  Gln  Asp  Asp  Thr  Lys  Thr  Leu  Ile  Lys  Thr  (b)
1              5                        10                       15
Ile  Val  Thr  Arg  Ile  Ser  Asp  Ile  Ser  His  Met  Gln  Ser  Val  Ser  Ser
               20                        25                       30
Lys  Gln  Arg  Val  Thr  Gly  Leu  Asp  Phe  Ile  Pro  Gly  Leu  His  Pro  Val
          35                        40                       45
Leu  Ser  Leu  Ser  Lys  Met  Asp  Gln  Thr  Leu  Ala  Ile  Tyr  Gln  Gln  Ile
     50                        55                       60
Leu  Thr  Ser  Leu  Pro  Ser  Arg  Asn  Val  Ile  Gln  Ile  Ser  Asn  Asp  Leu
65                        70                       75                       80
Glu  Asn  Leu  Arg  Asp  Leu  Leu  His  Leu  Leu  Ala  Ser  Ser  Lys  Ser  Cys
                    85                        90                       95
Pro  Leu  Pro  Gln  Ala  Arg  Ala  Leu  Glu  Thr  Leu  Glu  Ser  Leu  Gly  Gly
               100                       105                      110
Val  Leu  Glu  Ala  Ser  Leu  Tyr  Ser  Thr  Glu  Val  Val  Ala  Leu  Ser  Arg
          115                       120                      125
Leu  Gln  Gly  Ala  Leu  Gln  Asp  Met  Leu  Arg  Gln  Leu  Asp  Leu  Ser  Pro
     130                       135                      140
Gly  Cys
145
```

; (SEQ ID NO:2)

```
Val  Pro  Ile  Cys  Lys  Val  Gln  Asp  Asp  Thr  Lys  Thr  Leu  Ile  Lys  Thr  (c)
1              5                        10                       15
Ile  Val  Thr  Arg  Ile  Asn  Asp  Ile  Ser  His  Thr  Xaa  Ser  Val  Ser  Ser
               20                        25                       30
Lys  Gln  Arg  Val  Thr  Gly  Leu  Asp  Phe  Ile  Pro  Gly  Leu  His  Pro  Leu
          35                        40                       45
Leu  Ser  Leu  Ser  Lys  Met  Asp  Gln  Thr  Leu  Ala  Ile  Tyr  Gln  Gln  Ile
     50                        55                       60
Leu  Thr  Ser  Leu  Pro  Ser  Arg  Asn  Val  Val  Gln  Ile  Ser  Asn  Asp  Leu
65                        70                       75                       80
Glu  Asn  Leu  Arg  Asp  Leu  Leu  His  Leu  Leu  Ala  Ala  Ser  Lys  Ser  Cys
                    85                        90                       95
Pro  Leu  Pro  Gln  Val  Arg  Ala  Leu  Glu  Ser  Leu  Glu  Ser  Leu  Gly  Val
               100                       105                      110
Val  Leu  Glu  Ala  Ser  Leu  Tyr  Ser  Thr  Glu  Val  Val  Ala  Leu  Ser  Arg
          115                       120                      125
Leu  Gln  Gly  Ser  Leu  Gln  Asp  Met  Leu  Arg  Gln  Leu  Asp  Leu  Ser  Pro
     130                       135                      140
Gly  Cys
145
``` wherein Xaa at position 28 is Gln or absent; (SEQ ID NO:3)

```
Val  Pro  Ile  Gln  Lys  Val  Gln  Asp  Asp  Thr  Lys  Thr  Leu  Ile  Lys  Thr  (d)
1              5                        10                       15
Ile  Val  Thr  Arg  Ile  Asn  Asp  Ile  Ser  His  Xaa  Xaa  Ser  Val  Ser  Ser
               20                        25                       30
Lys  Gln  Lys  Val  Thr  Gly  Leu  Asp  Phe  Ile  Pro  Gly  Leu  His  Pro  Ile
          35                        40                       45
Leu  Thr  Leu  Ser  Lys  Met  Asp  Gln  Thr  Leu  Ala  Val  Tyr  Gln  Gln  Ile
     50                        55                       60
Leu  Thr  Ser  Met  Pro  Ser  Arg  Asn  Val  Ile  Gln  Ile  Ser  Asn  Asp  Leu
65                        70                       75                       80
Glu  Asn  Leu  Arg  Asp  Leu  Leu  His  Val  Leu  Ala  Phe  Ser  Lys  Ser  Cys
                    85                        90                       95
His  Leu  Pro  Trp  Ala  Ser  Gly  Leu  Glu  Thr  Leu  Asp  Ser  Leu  Gly  Gly
               100                       105                      110
```

Val Leu Glu Ala Ser Gly Tyr Ser Thr Glu Val Val Ala Leu Ser Arg
                115                 120                 125
Leu Gln Gly Ser Leu Gln Asp Met Leu Trp Gln Leu Asp Leu Ser Pro
    130                 135                 140
145
Gly Cys wherein:
  Xaa at position 27 is Thr or Ala; and
  Xaa at position 28 is Gln or absent; (SEQ ID NO:4)

Val Pro Ile Gln Lys Val Gln Ser Asp Thr Lys Thr Leu Ile Lys    (e)
1           5                   10                  15
Thr Ile Val Thr Arg Ile Asn Asp Ile Ser His Thr Gln Ser Val
            20                  25                  30
Ser Ser Lys Gln Arg Val Thr Gly Leu Asp Phe Ile Pro Gly Leu
            35                  40                  45
His Pro Val Leu Thr Leu Ser Gln Met Asp Gln Thr Leu Ala Ile
            50                  55                  60
Tyr Gln Gln Ile Leu Ile Asn Leu Pro Ser Arg Asn Val Ile Gln
            65                  70                  75
Ile Ser Asn Asp Leu Glu Asn Leu Arg Asp Leu Leu His Leu Leu
            80                  85                  90
Ala Phe Ser Lys Ser Cys His Leu Pro Leu Ala Ser Gly Leu Glu
            95                  100                 105
Thr Leu Glu Ser Leu Gly Asp Val Leu Glu Ala Ser Leu Tyr Ser
            110                 115                 120
Thr Glu Val Val Ala Leu Ser Arg Leu Gln Gly Ser Leu Gln Asp
            125                 130                 135
Met Leu Trp Gln Leu Asp Leu Ser Pro Gly Cys
            140                 145        ; (SEQ ID NO:5)

Val Pro Ile His Lys Val Gln Asp Asp Thr Lys Thr Leu Ile Lys Thr    (f)
1           5                   10                  15
Ile Val Thr Arg Ile Asn Asp Ile Ser His Thr Gln Ser Val Ser Ala
            20                  25                  30
Arg Gln Arg Val Thr Gly Leu Asp Phe Ile Pro Gly Leu His Pro Ile
            35                  40                  45
Leu Ser Leu Ser Lys Met Asp Gln Thr Leu Ala Val Tyr Gln Gln Ile
            50                  55                  60
Leu Thr Ser Leu Pro Ser Gln Asn Val Leu Gln Ile Ala His Asp Leu
65                  70                  75                  80
Glu Asn Leu Arg Asp Leu Leu His Leu Leu Ala Phe Ser Lys Ser Cys
            85                  90                  95
Ser Leu Pro Gln Thr Arg Gly Leu Gln Lys Pro Glu Ser Leu Asp Gly
            100                 105                 110
Val Leu Glu Ala Ser Leu Tyr Ser Thr Glu Val Val Ala Leu Ser Arg
            115                 120                 125
Leu Gln Gly Ser Leu Gln Asp Ile Leu Gln Gln Leu Asp Leu Ser Pro
            130                 135                 140
Glu Cys
145         , (SEQ ID NO:5)

Val Pro Ile Gln Lys Val Gln Asp Asp Thr Lys Thr Leu Ile Lys Thr    (g)
1           5                   10                  15
Ile Val Thr Arg Ile Xaa Asp Ile Ser His Xaa Xaa Ser Val Ser Ser
            20                  25                  30
Lys Gln Lys Val Thr Gly Leu Asp Phe Ile Pro Gly Leu His Pro Ile
            35                  40                  45
Leu Thr Leu Ser Lys Xaa Asp Gln Thr Leu Ala Val Tyr Gln Gln Ile
            50                  55                  60
Leu Thr Ser Xaa Pro Ser Arg Xaa Val Ile Gln Ile Xaa Asn Asp Leu
65                  70                  75                  80
Glu Asn Leu Arg Asp Leu Leu His Val Leu Ala Phe Ser Lys Ser Cys
            85                  90                  95
His Leu Pro Trp Ala Ser Gly Leu Glu Thr Leu Asp Ser Leu Gly Gly
            100                 105                 110
Val Leu Glu Ala Ser Xaa Tyr Ser Thr Glu Val Val Ala Leu Ser Arg
            115                 120                 125
Leu Gln Gly Ser Leu Gln Asp Met Leu Trp Gln Leu Asp Leu Ser Pro
            130                 135                 140
145
Gly Cys wherein:
  Xaa at position 22 is Asn, Asp or Glu;
  Xaa at position 27 is Thr or Ala;
  Xaa at position 28 is Gln, Glu, or absent;
  Xaa at position 54 is Met or Ala;
  Xaa at position 68 is Met or Leu;
  Xaa at position 72 Asn, Asp or Glu;
  Xaa at position 77 is Ser or Ala;
  Xaa at position 118 is Gly or Leu;
  said protein having at least one substitution selected from the group consisting of:
  His at position 97 is replaced with Ser or Pro;
  Trp at position 100 is replaced with Gln, Ala or Leu;
  Ala at position 101 is replaced with Thr or Val;
  Ser at position 102 is replaced with Arg;
  Gly at position 103 is replaced with Ala;
  Glu at position 105 is replaced with Gln;
  Thr at position 106 is replaced with Lys or Ser;
  Leu at position 107 is replaced with Pro;
  Asp at position 108 is replaced with Glu; or
  Gly at position 111 is replaced with Asp; and, (SEQ ID NO:7)

Val Pro Ile Gln Lys Val Gln Asp Asp Thr Lys Thr Leu Ile Lys Thr    (h)
1           5                   10                  15
Ile Val Thr Arg Ile Asn Asp Ile Ser His Xaa Gln Ser Val Ser Ser
            20                  25                  30

-continued

| | | | | | | | | | | | | | | |
|---|---|---|---|---|---|---|---|---|---|---|---|---|---|---|
| Lys | Gln | Lys<br>35 | Val | Thr | Gly | Leu | Asp<br>40 | Phe | Ile | Pro | Gly | Leu<br>45 | His | Pro | Ile |
| Leu | Thr<br>50 | Leu | Ser | Lys | Met | Asp<br>55 | Gln | Thr | Leu | Ala | Val<br>60 | Tyr | Gln | Gln | Ile |
| Leu<br>65 | Thr | Ser | Met | Pro | Ser<br>70 | Arg | Asn | Val | Ile | Gln<br>75 | Ile | Xaa | Asn | Asp | Leu<br>80 |
| Glu | Asn | Leu | Arg | Asp<br>85 | Leu | Leu | His | Val | Leu<br>90 | Ala | Phe | Ser | Lys | Ser<br>95 | Cys |
| His | Leu | Pro | Trp<br>100 | Ala | Ser | Gly | Leu | Glu<br>105 | Thr | Leu | Asp | Ser | Leu<br>110 | Gly | Gly |
| Val | Leu | Glu<br>115 | Ala | Ser | Xaa | Tyr | Ser<br>120 | Thr | Glu | Val | Val | Ala<br>125 | Leu | Ser | Arg |
| Leu | Gln<br>130 | Gly | Ser | Leu | Gln | Asp<br>135 | Met | Leu | Trp | Gln | Leu<br>140 | Asp | Leu | Ser | Pro |
| 145<br>Gly | Cys | | | | | | | | | | | | | | | wherein:

Xaa at position 27 is Thr or Ala;

Xaa at position 77 is Ser or Ala;

Xaa at position 118 is Gly or Leu;

said protein having at least one substitution, preferably having one to five substitutions and, most preferably, one to two substitutions selected from the group consisting of:

His at position 97 is replaced with Ser;

Trp at position 100 is replaced with Gln;

Ala at position 101 is replaced with Thr;

Glu at position 105 is replaced with Gln;

Thr at position 106 is replaced with Lys;

Leu at position 107 is replaced with Pro;

Asp at position 108 is replaced with Glu; or

Gly at position 111 is replaced with Asp, (SEQ ID NO:8) or a pharmaceutically acceptable salt or solvate thereof.

3. A method of claim 1 wherein said obese type II diabetic has endogenous leptin levels in the range of 0 to 80 ng/ml.

4. A method of claim 1 wherein said obese type II diabetic has endogenous leptin levels in the range of 0 to 50 ng/ml.

5. A method of claim 1 wherein said obese type II diabetic has endogenous leptin levels in the range of 0 to 30 ng/ml.

6. A method of claim 1 wherein said obese type II diabetic has endogenous leptin levels in the range of 0 to 15 ng/ml.

7. A method for treating or ameliorating diabetes mellitus which comprises administering to an afflicted patient a leptin or leptin mimetic.

* * * * *